(12) United States Patent
Julius et al.

(10) Patent No.: US 8,728,757 B2
(45) Date of Patent: *May 20, 2014

(54) METHODS OF MODULATING COLD SENSORY PERCEPTION VIA A COLD- AND MENTHOL-SENSITIVE RECEPTOR (CMR1)

(71) Applicant: The Regents of the University of California, Oakland, CA (US)

(72) Inventors: David Julius, San Francisco, CA (US); David D. McKemy, Seal Beach, CA (US); Werner M. Neuhausser, Jamaica Plain, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,561

(22) Filed: May 24, 2013

(65) Prior Publication Data
US 2013/0315833 A1 Nov. 28, 2013

Related U.S. Application Data

(60) Continuation of application No. 13/340,443, filed on Dec. 29, 2011, now Pat. No. 8,470,545, which is a division of application No. 12/905,001, filed on Oct. 14, 2010, now Pat. No. 8,361,733, which is a division of application No. 12/032,485, filed on Feb. 15, 2008, now Pat. No. 7,838,253, which is a division of application No. 10/352,724, filed on Jan. 27, 2003, now Pat. No. 7,371,841.

(60) Provisional application No. 60/351,974, filed on Jan. 25, 2002, provisional application No. 60/355,037, filed on Feb. 7, 2002.

(51) Int. Cl.
*C12Q 1/02* (2006.01)
*G01N 33/53* (2006.01)
*G01N 33/567* (2006.01)

(52) U.S. Cl.
USPC .............................. 435/29; 435/7.2; 435/7.21

(58) Field of Classification Search
None
See application file for complete search history.

(56) References Cited

U.S. PATENT DOCUMENTS 6,194,152 B1 2/2001 Laus et al.
7,063,959 B1 6/2006 Scharenberg

FOREIGN PATENT DOCUMENTS

| WO | WO 99/09166 A2 | 2/1999 |
| WO | WO 00/40614 A2 | 7/2000 |
| WO | WO 01/51633 A2 | 7/2001 |
| WO | WO 01/73032 A2 | 10/2001 |
| WO | WO 02/101045 A2 | 12/2002 |
| WO | WO 03/087158 A2 | 10/2003 |
| WO | WO 03/102156 A2 | 12/2003 |

OTHER PUBLICATIONS

Clapham, David E. et al.; "The TRP ION Channel Family"; 2001, *Nature Reviews*, vol. 2, pp. 387-395.
McKemy, Werner M., et al.; "Identification of a cold receptor reveals a general role for TRP channels in thermosensation"; *Nature*, 2002, vol. 416, pp. 52-58.
Peier, Andrea M., et al.; "A TRP Channel that Senses Cold Stimuli and Menthol"; *Cell*, 2002, vol. 108, pp. 705-715.
Seydel, Caroline; "How Neurons know that it's C-c-c-c-cold Outside"; *Science*, 2002, vol. 295, pp. 1451-1452.
Szallasi, Arpad; "The Vanilloid (Capsaicin) Receptor: Receptor Types and Species Differences"; 1994, *Gen. Pharmac*, vol. 25, No. 2, pp. 223-243.

*Primary Examiner* — Robert Landsman
(74) *Attorney, Agent, or Firm* — Kilpatrick Townsend & Stockton LLP

(57) ABSTRACT

The present invention relates to regulation of cold sensation and pain. More particularly, the present invention is directed to nucleic acids encoding a member of the transient regulatory protein family, CMR1, which is involved in modulation of the perception of cold sensations and pain. The invention further relates to methods for identifying and using agents that modulate cold responses and pain responses stimulated by cold via modulation of CMR1 and CMR1-related signal transduction.

19 Claims, 7 Drawing Sheets

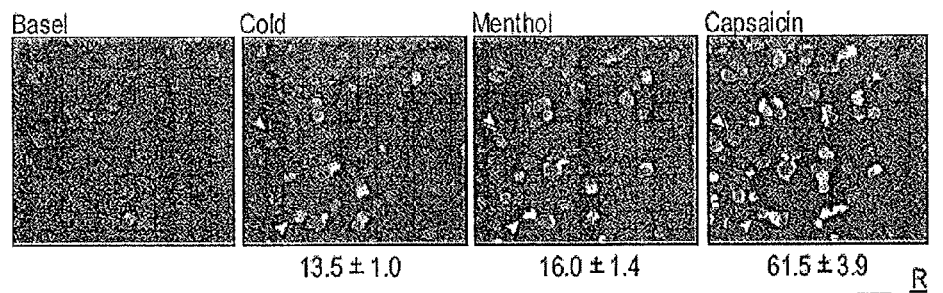
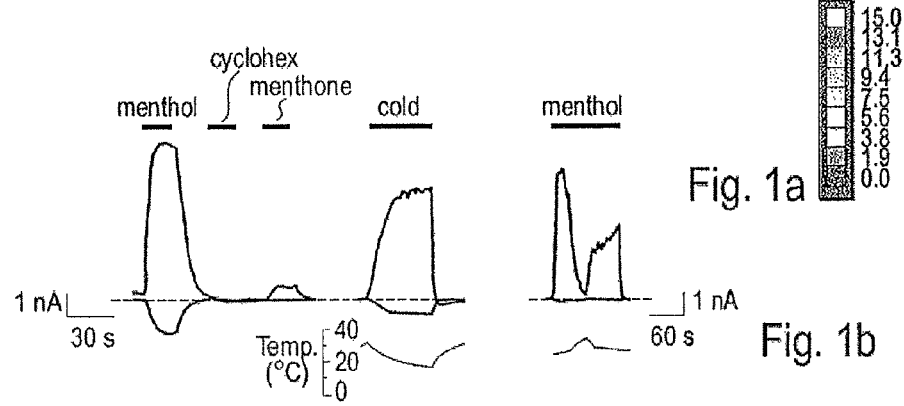
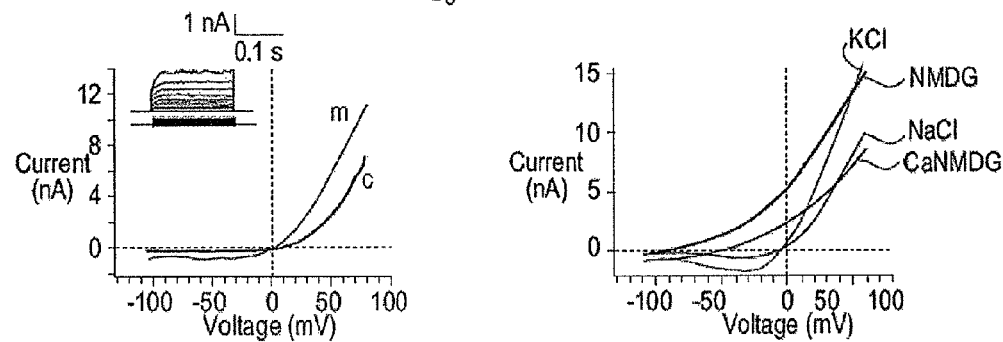
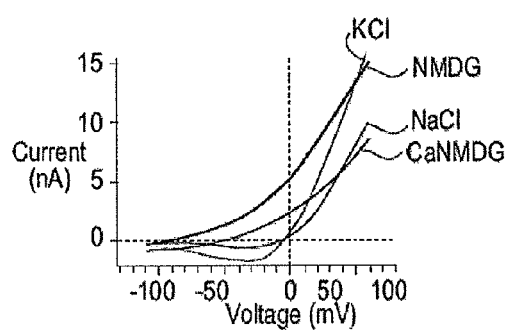
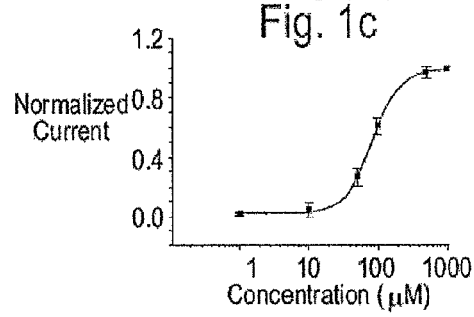
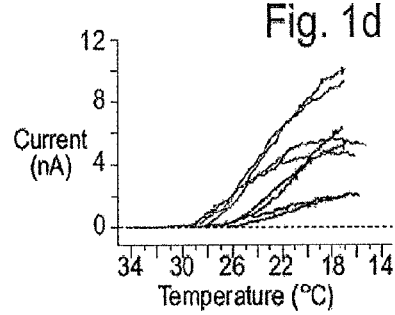

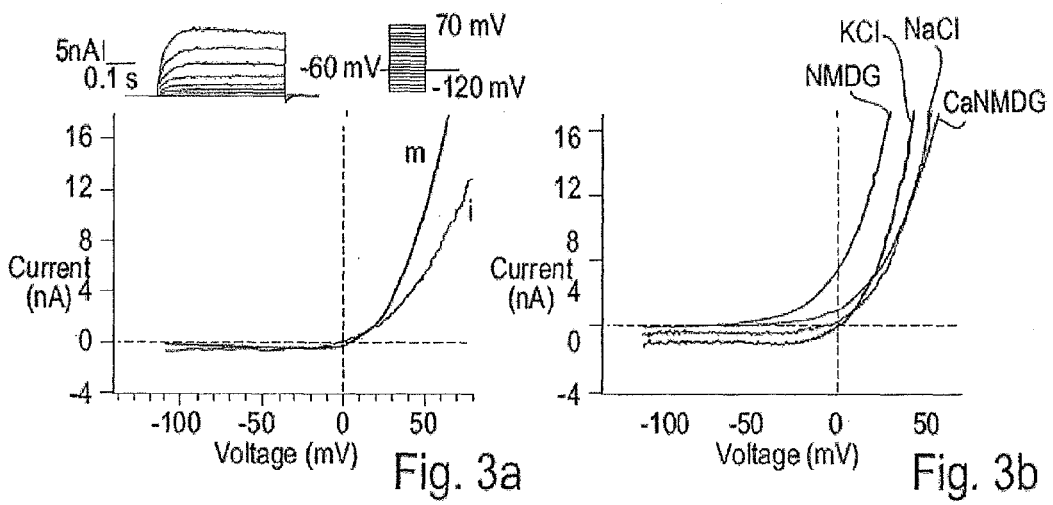
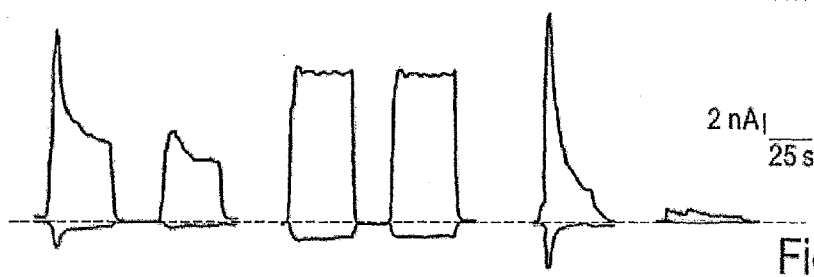
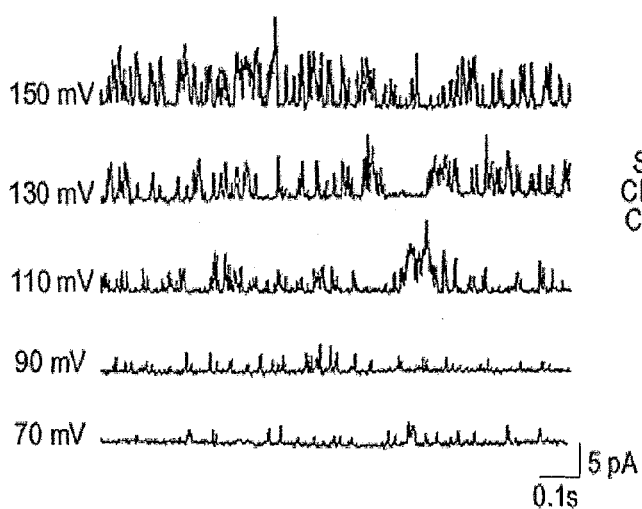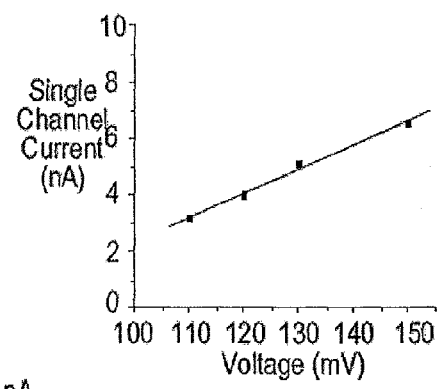
Fig. 3a  Fig. 3b  Fig. 3c  Fig. 3d  Fig. 3e MSFEGARLSMRSRRNGTLGSTRTLYSSVSRSTDVSYSESDLVNFIQANPK 50
KRECVFFTRDSKAMESICKCGYAQSQHIEGTQINQNEKWNYKKHTKEFPT 100
DAFGDIQFETLGKKGKYLRLSCDTDSETLYELLTQHWHLKTPNLVISVTG 150
GAKNFALKPRMRKJFSRLIYIAQSKGAWILTGGTHYGLMKYIGEVVRDNT 200
ISRNSEENIVAIGIAAWGMVSNRDTLIRNCDDEGHFSAQYIMDDFMRDPL 250
YILDNNHTHLLLVDNGCHGHPTVEAKLRNQLEKYISERTSQDSNYGGKIP 300
IVCFAQGGGRETLKAINTSVKSKIPCVVVEGSGQIADVIASLVEVEDVLT 350
SSMVKEKLVRFLPRTVSRLPEEEIESWIKWLKEILESPHLLTVIKMEEAG 400
DEVVSSAISYALYKAFSTNEQDKDNWNGQLKLLLEWNQLDLASDEIFTHD 450
RRWESADLQEVMFTALIKDRPKFVRLFLENGLNLQKFLTNEVLTELFSTH 500
FSTLVYRNLQIAKNSYNDALLTFVWKLVANFRRSFWKEDRSSREDLDVEL 550
HDASLTTRHPLQALFIWAILQNKKELSKVIWEQTKGCTLAALGASKLLKT 600
LAKVKNDINAAGESEELANEYETRAVELFTECYSSDEDLAEQLLVYSCEA 650

S1
WGGSNCLELAVEATDQHFIAQPGVQNFLSKQWYGEISRD [TKNWKIILCLF] 700
                                              S2
[IIPLVGCGLV] SFRKKPIDKHKKLLWYYVAFFTS [PFVVFSWNVVFYIAFLL] 750

[LFAYVLLM] DFHSVPHTPELILYALVFVLFCDEVRQWYMNGVNYFTDLWNV 800
    S3                                   S4
MD [TLGLFYFIAGIVFRLHS] SNKSSLYSGR [VIFCLDYIIFTLRLIHIFT] VS 850
                 S5
RNLGPKIIMLQRMLID [VFFLFLFAVWMVAFGVAR] QGILRQNEQRWRWIF 900

RSVIYEPYLAMFGQVPSDVDSTTYDFSHCTFSGNESKPLCVELDEYNLPR 950
       S6
FPEW [ITIPLVCIYMLSTNILLVNLLVA] MFGYTVGIVQENNDQDVWKFQRYF 1000

LIQEYCNRLNIPFPFVVFAYFYMVVKKCFKCCCKEKNTESSACCFRNEDN 1050
ETLAWEGVMKENYLVKINTKANDNAEEMRHRFRQLDTKLNDLKGLLKEIA 1100
NKIK                                              1104

Fig. 5a

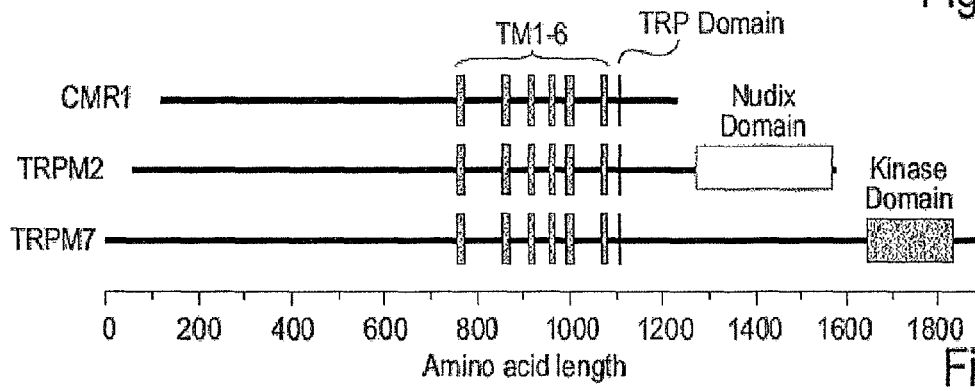

Fig. 5b

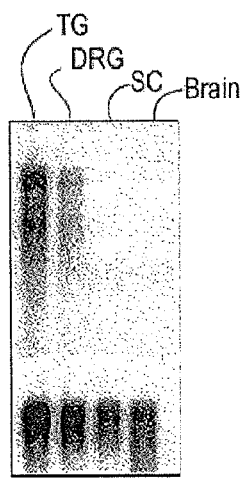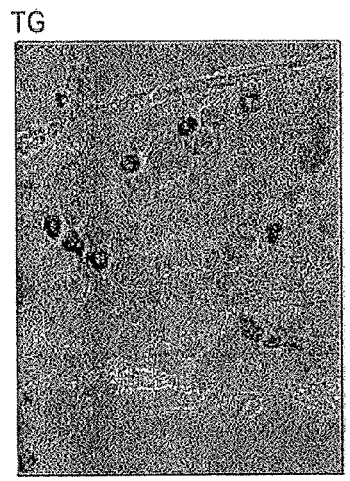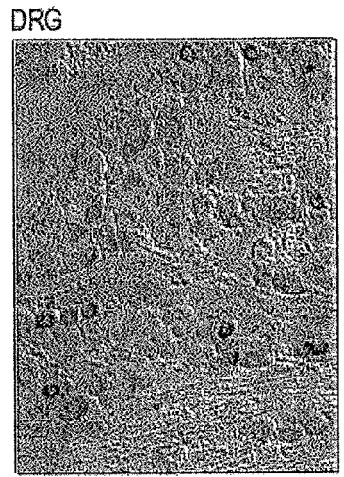
Fig. 6a                    Fig. 6b

SEQUENCE LISTING

<160> NUMBER OF SEQ ID NOS: 5

<210> SEQ ID NO 1
<211> LENGTH: 1104
<212> TYPE: PRT
<213> ORGANISM: Rattus sp.

<400> SEQUENCE: 1

```
Met Ser Phe Glu Gly Ala Arg Leu Ser Met Arg Ser Arg Arg Asn Gly
 1               5                  10                  15

Thr Leu Gly Ser Thr Arg Thr Leu Tyr Ser Ser Val Ser Arg Ser Thr
            20                  25                  30

Asp Val Ser Tyr Ser Glu Ser Asp Leu Val Asn Phe Ile Gln Ala Asn
        35                  40                  45

Phe Lys Lys Arg Glu Cys Val Phe Phe Thr Arg Asp Ser Lys Ala Met
    50                  55                  60

Glu Ser Ile Cys Lys Cys Gly Tyr Ala Gln Ser Gln His Ile Glu Gly
 65                  70                  75                  80

Thr Gln Ile Asn Gln Asn Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Leu Arg Leu Ser Cys Asp Thr Asp Ser Glu Thr
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Asp Glu Gly His Phe Ser Ala Gln Tyr
225                 230                 235                 240

Ile Met Asp Asp Phe Met Arg Asp Pro Leu Tyr Ile Leu Asp Asn Asn
                245                 250                 255

His Thr His Leu Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285

Thr Ser Gln Asp Ser Asn Tyr Gly Gly Lys Ile Pro Ile Val Cys Phe
    290                 295                 300

Ala Gln Gly Gly Gly Arg Glu Thr Leu Lys Ala Ile Asn Thr Ser Val
305                 310                 315                 320

Lys Ser Lys Ile Pro Cys Val Val Val Glu Gly Ser Gly Gln Ile Ala
                325                 330                 335

Asp Val Ile Ala Ser Leu Val Glu Val Glu Asp Val Leu Thr Ser Ser
            340                 345                 350

Met Val Lys Glu Lys Leu Val Arg Phe Leu Pro Arg Thr Val Ser Arg
        355                 360                 365
```

-continued

```
Leu Pro Glu Glu Glu Ile Glu Ser Trp Ile Lys Trp Leu Lys Glu Ile
    370                 375                 380

Leu Glu Ser Pro His Leu Leu Thr Val Ile Lys Met Glu Glu Ala Gly
385                 390                 395                 400

Asp Glu Val Val Ser Ser Ala Ile Ser Tyr Ala Leu Tyr Lys Ala Phe
                    405                 410                 415

Ser Thr Asn Glu Gln Asp Lys Asp Asn Trp Asn Gly Gln Leu Lys Leu
            420                 425                 430

Leu Leu Glu Trp Asn Gln Leu Asp Leu Ala Ser Asp Glu Ile Phe Thr
        435                 440                 445

His Asp Arg Arg Trp Glu Ser Ala Asp Leu Gln Glu Val Met Phe Thr
    450                 455                 460

Ala Leu Ile Lys Asp Arg Pro Lys Phe Val Arg Leu Phe Leu Glu Asn
465                 470                 475                 480

Gly Leu Asn Leu Gln Lys Phe Leu Thr Asn Glu Val Leu Thr Glu Leu
                    485                 490                 495

Phe Ser Thr His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
        515                 520                 525

Ala Asn Phe Arg Arg Ser Phe Trp Lys Glu Asp Arg Ser Ser Arg Glu
    530                 535                 540

Asp Leu Asp Val Glu Leu His Asp Ala Ser Leu Thr Thr Arg His Pro
545                 550                 555                 560

Leu Gln Ala Leu Phe Ile Trp Ala Ile Leu Gln Asn Lys Lys Glu Leu
                    565                 570                 575

Ser Lys Val Ile Trp Glu Gln Thr Lys Gly Cys Thr Leu Ala Ala Leu
            580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
    610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                    645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
    690                 695                 700

Val Gly Cys Gly Leu Val Ser Phe Arg Lys Lys Pro Ile Asp Lys His
705                 710                 715                 720

Lys Lys Leu Leu Trp Tyr Tyr Val Ala Phe Phe Thr Ser Pro Phe Val
                    725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Thr Pro Glu
        755                 760                 765

Leu Ile Leu Tyr Ala Leu Val Phe Val Leu Phe Cys Asp Glu Val Arg
    770                 775                 780

Gln Trp Tyr Met Asn Gly Val Asn Tyr Phe Thr Asp Leu Trp Asn Val
```

```
                785                 790                 795                 800
Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830

Cys Leu Asp Tyr Ile Ile Phe Thr Leu Arg Leu Ile His Ile Phe Thr
        835                 840                 845

Val Ser Arg Asn Leu Gly Pro Lys Ile Ile Met Leu Gln Arg Met Leu
    850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
            900                 905                 910

Gly Gln Val Pro Ser Asp Val Asp Ser Thr Thr Tyr Asp Phe Ser His
        915                 920                 925

Cys Thr Phe Ser Gly Asn Glu Ser Lys Pro Leu Cys Val Glu Leu Asp
    930                 935                 940

Glu Tyr Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Ile Val Gln Glu Asn Asn Asp Gln
            980                 985                 990

Val Trp Lys Phe Gln Arg Tyr Phe Leu Val Gln Glu Tyr Cys Asn Arg
        995                 1000                1005

Leu Asn Ile Pro Phe Pro Phe Val Val Phe Ala Tyr Phe Tyr Met Val
    1010                1015                1020

Val Lys Lys Cys Phe Lys Cys Cys Cys Lys Glu Lys Asn Thr Glu Ser
1025                1030                1035                1040

Ser Ala Cys Cys Phe Arg Asn Glu Asp Asn Glu Thr Leu Ala Trp Glu
            1045                1050                1055

Gly Val Met Lys Glu Asn Tyr Leu Val Lys Ile Asn Thr Lys Ala Asn
        1060                1065                1070

Asp Asn Ala Glu Glu Met Arg His Arg Phe Arg Gln Leu Asp Thr Lys
    1075                1080                1085

Leu Asn Asp Leu Lys Gly Leu Leu Lys Glu Ile Ala Asn Lys Ile Lys
    1090                1095                1100

<210> SEQ ID NO 2
<211> LENGTH: 3315
<212> TYPE: DNA
<213> ORGANISM: Rattus sp.

<400> SEQUENCE: 2
atgtccttcg agggagccag gctcagcatg aggagccgca gaaatggaac tctgggcagc      60
acccggaccc tgtactccag cgtgtctcgg agcacagacg tgtcctacag tgaaagtgat     120
ttggtgaatt ttattcaggc aaattttaaa aaacgagaat cgtcttctt taccagagac      180 tccaaggcca tggagagcat atgcaagtgt ggttatgccc agagccagca tatcgaaggc     240
acccagatca accaaaatga gaagtggaac tacaaaaaac acaccaagga gtttccaaca     300
gacgcctttg ggacattca gtttgagact ctggggaaga aaggcaagta cttacgctta     360
tcctgtgaca cggactctga aaccctctac gaactgctga cccagcactg gcacctcaaa     420
```

```
acacccaacc tggtcatctc agtgacgggt ggagccaaaa actttgcttt gaagccacgc    480
atgcgcaaaa tcttcagtcg gctgatctac atcgctcagt ctaaaggggc atggattctt    540
accggaggca ctcattacgg tctgatgaag tacataggtg aagtggtgag ggataacacc    600
atcagcagga actcggaaga gaacatcgtg gccattggca tagcggcctg gggcatggtc    660
tccaacaggg acaccctcat caggaattgt gatgatgagg acattttttc agctcaatat    720
atcatggatg acttcatgag agatcctctc tacatcctgg acaacaatca tacccacctg    780
ctgcttgtgg acaacggttg tcatggacac cccacggtgg aagccaaact tcggaatcag    840
ctggagaagt acatctctga gcgcaccagt caagattcca actatggtgg taagatcccc    900
atcgtgtgtt ttgcccaggg aagtggaaga gaaactttga aagccatcaa cacctctgtc    960
aaaagtaaga tcccctgtgt ggtggtggaa ggctcggggc agattccga tgtgattgcc   1020
agcctggtgg aggtagagga tgttttaacc tcttccatgg tcaaagagaa gctggtacgg   1080
tttttacccc gcactgtgtc ccggctgcct gaagaggaga ttgagagctg gatcaaatgg   1140
ctcaaagaaa ttcttgagag cccccacctc ctcacggtca tcaagatgga ggaggctgga   1200
gacgaggtcg tgagcagcgc catttcctac gcgctgtaca aagccttcag cactaatgaa   1260
caagacaagg acaactggaa cggacagctg aagcttctgc tggagtggaa ccaactggac   1320
cttgccagtg atgagatctt cacccatgac cgccgctggg agtctgccga ccttcaggaa   1380
gtcatgttca cggccctcat aaaggacagg cccaagtttg tccgcctctt cctggagaat   1440
ggcctcaacc tgcagaagtt cctcaccaat gaagtcctca cggagctctt ctccacccac   1500
ttcagcaccc tagtgtaccg gaacctgcag atcgccaaga actcctacaa cgatgcactc   1560
cttacctttg tctggaagtt ggtggcaaac ttccgtagaa gcttctggaa agaggacaga   1620
agcagcaggg aggacttgga tgtggaactc catgatgcat ctctcaccac ccggcacccc   1680
ctgcaggctc ttttcatctg gccattctt cagaacaaga aggaactctc caaggtcatc   1740
tgggagcaaa ccaaaggctg tactctggcc gccttggggg ccagcaaact tctgaagacc   1800
ctggccaaag ttaagaatga tatcaacgca gctggggaat ctgaggaact ggctaatgag   1860
tatgagaccc gagcagtgga gttgttcact gagtgttaca gcagtgatga ggacttggca   1920
gaacagctac tggtctactc ttgtgaagcc tggggtggga gcaactgtct ggagctggcg   1980
gtggaggcta cggaccagca tttcattgct cagcctgggg tccagaattt cctttctaag   2040
caatggtatg gagagatttc ccgagacacg aagaactgga agattatcct gtgtctgttc   2100
atcatccccc tggtgggctg tggcctcgta tcgtttagga agaagcccat tgacaagcac   2160
aagaagctgc tctggtacta cgtggccttc ttcacttcgc ccttcgtggt cttctcctgg   2220
aacgtggtct tctacatcgc cttcctcctg ctgtttgcgt atgtgctgct catggacttc   2280
cactcggtgc acacaccccc cgagctgatc ctctatgccc tggtcttcgt cctcttctgt   2340
gatgaagtga ggcagtggta catgaacgga gtgaattatt tcaccgacct atggaacgtt   2400
atggacacac tgggactttt ctacttcata gcgggtattg tattccggct tcactcttca   2460
aataaaagct ctttgtactc cggcgagtc atttttctgtc tggattacat tatattcact   2520
ctaaggctca tccacatttt caccgtgagc aggaacctgg acccaagat tataatgctg   2580
cagcggatgc tcatcgacgt tttcttcttc ttgtttctct ttgctgtgtg gatggtggcc   2640
ttcggcgtag ccagacaggg gatccttagg caaaatgaac agcgctggag gtggatcttc   2700
cgctctgtca tctatgagcc ctacctggcc atgtttggcc aggtgccag tgatgtggac   2760
agtaccacat atgacttctc ccactgcacc ttctcgggaa atgagtccaa gccactgtgc   2820
```

```
gtggagctag atgaatacaa tctgccccgc ttccctgagt ggatcaccat cccactagtg    2880
tgcatctaca tgctctccac caacatcctt ctggtcaatc tcctggtcgc catgtttggc    2940
tacacggtgg gcattgtgca ggagaacaac gatcaggtct ggaagttcca gcggtacttc    3000
ctggtgcagg agtactgcaa ccgcctcaac atccccttcc ccttcgtcgt cttcgcttac    3060
ttctacatgg tggtcaagaa gtgtttcaaa tgctgctgta agagaagaa cacggagtct    3120 tctgcctgct gtttcagaaa tgaggacaac gagactttgg cgtgggaggg cgtcatgaag    3180
gagaattacc ttgtcaagat caacacgaag gccaacgaca acgcagagga gatgaggcat    3240
cggttcagac aactggacac aaagcttaat gatctcaaag gtcttctgaa agagattgct    3300
aataaaatca aataa                                                     3315
```

<210> SEQ ID NO 3
<211> LENGTH: 1104
<212> TYPE: PRT
<213> ORGANISM: Homo sapiens
<220> FEATURE:
<221> NAME/KEY: MOD_RES
<222> LOCATION: (1)..(1104)
<223> OTHER INFORMATION: Xaa = any amino acid

<400> SEQUENCE: 3

```
Met Ser Phe Arg Ala Ala Arg Leu Ser Met Arg Asn Arg Arg Asn Asp
  1               5                  10                  15

Thr Leu Asp Ser Thr Arg Thr Leu Tyr Ser Ser Ala Ser Arg Ser Thr
             20                  25                  30

Asp Leu Ser Tyr Ser Glu Ser Asp Leu Val Asn Phe Ile Gln Ala Asn
         35                  40                  45

Phe Lys Lys Arg Glu Cys Val Phe Phe Thr Lys Asp Ser Lys Ala Thr
     50                  55                  60

Glu Asn Val Cys Lys Cys Gly Tyr Ala Gln Ser Gln His Met Glu Gly
 65                  70                  75                  80

Thr Gln Ile Asn Gln Ser Glu Lys Trp Asn Tyr Lys Lys His Thr Lys
                 85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Ser Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Ala Glu Gly Tyr Phe Leu Ala Gln Tyr
225                 230                 235                 240

Leu Met Asp Asp Phe Thr Arg Asp Pro Leu Tyr Ile Leu Asp Asn Asn
                245                 250                 255

His Thr His Leu Leu Leu Val Asp Asn Gly Cys His Gly His Pro Thr
```

-continued

```
                260                 265                 270
Val Glu Ala Lys Leu Arg Asn Gln Leu Glu Lys Tyr Ile Ser Glu Arg
                275                 280                 285

Thr Ile Gln Asp Ser Asn Tyr Gly Gly Lys Ile Pro Ile Val Cys Phe
290                 295                 300

Ala Gln Gly Gly Gly Lys Glu Thr Leu Lys Ala Ile Asn Thr Ser Ile
305                 310                 315                 320

Lys Asn Lys Ile Pro Cys Val Val Glu Gly Ser Gly Gln Ile Ala
                325                 330                 335

Asp Val Ile Ala Ser Leu Val Glu Val Glu Asp Ala Leu Thr Ser Ser
                340                 345                 350

Ala Val Lys Glu Lys Leu Val Arg Phe Leu Pro Arg Thr Val Ser Arg
                355                 360                 365

Leu Pro Glu Glu Glu Thr Glu Ser Trp Ile Lys Trp Leu Lys Glu Ile
                370                 375                 380

Leu Glu Cys Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Ser Glu Gln Asp Lys Asp Asn Trp Asn Gly Gln Leu Lys Leu
                420                 425                 430

Leu Leu Glu Trp Asn Gln Leu Asp Leu Ala Asn Asp Glu Ile Phe Thr
                435                 440                 445

Asn Asp Arg Arg Trp Glu Ser Ala Asp Leu Gln Glu Val Met Phe Thr
                450                 455                 460

Ala Leu Ile Lys Asp Arg Pro Lys Phe Val Arg Leu Phe Leu Glu Asn
465                 470                 475                 480

Gly Leu Asn Pro Arg Lys Phe Leu Thr His Asp Val Leu Thr Glu Leu
                485                 490                 495

Phe Ser Asn His Phe Ser Thr Leu Val Tyr Arg Asn Leu Gln Ile Ala
                500                 505                 510

Lys Asn Ser Tyr Asn Asp Ala Leu Leu Thr Phe Val Trp Lys Leu Val
                515                 520                 525

Ala Asn Phe Arg Arg Gly Phe Arg Lys Glu Asp Arg Asn Gly Arg Asp
                530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
                580                 585                 590

Gly Ala Ser Lys Leu Leu Lys Thr Leu Ala Lys Val Lys Asn Asp Ile
                595                 600                 605

Asn Ala Ala Gly Glu Ser Glu Glu Leu Ala Asn Glu Tyr Glu Thr Arg
                610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
                660                 665                 670

Gly Val Gln Asn Phe Leu Ser Lys Gln Trp Tyr Gly Glu Ile Ser Arg
                675                 680                 685
```

-continued

```
Asp Thr Lys Asn Trp Lys Ile Ile Leu Cys Leu Phe Ile Ile Pro Leu
690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Thr Ser Pro Phe Val
            725                 730                 735

Val Phe Ser Trp Asn Val Val Phe Tyr Ile Ala Phe Leu Leu Leu Phe
        740                 745                 750

Ala Tyr Val Leu Leu Met Asp Phe His Ser Val Pro His Pro Pro Glu
        755                 760                 765

Leu Val Leu Tyr Ser Leu Val Phe Val Leu Phe Cys Asp Glu Val Arg
770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Xaa Val Phe Arg
                805                 810                 815

Leu His Ser Ser Asn Lys Ser Ser Leu Tyr Ser Gly Arg Val Ile Phe
                820                 825                 830

Cys Leu Asp Tyr Ile Ile Phe Thr Leu Arg Leu Ile His Ile Phe Thr
            835                 840                 845

Val Ser Arg Asn Leu Gly Pro Lys Ile Ile Met Leu Gln Arg Met Leu
850                 855                 860

Ile Asp Val Phe Phe Phe Leu Phe Leu Phe Ala Val Trp Met Val Xaa
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
            900                 905                 910

Gly Gln Val Pro Ser Asp Val Asp Gly Thr Thr Tyr Asp Phe Ala His
            915                 920                 925

Cys Thr Phe Thr Gly Asn Glu Ser Lys Pro Leu Cys Val Glu Xaa Asp
930                 935                 940

Glu His Xaa Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Thr Val Gln Glu Asn Asn Asp Gln
                980                 985                 990

Val Trp Lys Phe Gln Arg Tyr Phe Leu Val Gln Glu Xaa Cys Ser Arg
            995                 1000                1005

Leu Asn Ile Pro Phe Pro Phe Ile Val Phe Ala Tyr Phe Tyr Met Val
    1010                1015                1020

Val Lys Lys Cys Phe Lys Cys Cys Cys Lys Glu Lys Asn Met Glu Ser
1025                1030                1035                1040

Ser Val Cys Cys Phe Lys Asn Glu Asp Asn Glu Thr Leu Ala Trp Glu
                1045                1050                1055

Gly Val Met Lys Glu Asn Tyr Leu Val Lys Ile Asn Thr Lys Ala Asn
            1060                1065                1070

Asp Thr Ser Glu Glu Met Arg His Arg Phe Arg Gln Leu Asp Xaa Lys
    1075                1080                1085

Leu Asn Asp Leu Lys Gly Leu Leu Lys Glu Ile Ala Asn Lys Ile Lys
    1090                1095                1100
```

<210> SEQ ID NO 4

<211> LENGTH: 3315
<212> TYPE: DNA
<213> ORGANISM: Homo sapiens
<220> FEATURE:
<221> NAME/KEY: modified_base
<222> LOCATION: (1)..(3315)
<223> OTHER INFORMATION: n = g, a, c or t

<400> SEQUENCE: 4

| | | | | | |
|---|---|---|---|---|---|
| atgtcctttc | gggcagccag | gctcagcatg | aggaacagaa | ggaatgacac | tctggacagc | 60 |
| acccggaccc | tgtactccag | cgcgtctcgg | agcacagact | tgtcttacag | tgaaagcgac | 120 |
| ttggtgaatt | ttattcaagc | aaattttaag | aaacgagaat | gtgtcttctt | taccaaagat | 180 |
| tccaaggcca | cggagaatgt | gtgcaagtgt | ggctatgccc | agagccagca | catggaaggc | 240 |
| acccagatca | accaaagtga | gaaatggaac | tacaagaaac | acaccaagga | atttcctacc | 300 |
| gacgcctttg | gggatattca | gtttgagaca | ctggggaaga | aagggaagta | tatacgtctg | 360 |
| tcctgcgaca | cggacgcgga | aatcctttac | gagctgctga | cccagcactg | gcacctgaaa | 420 |
| acacccaacc | tggtcatttc | tgtgaccggg | ggcgccaaga | acttcgccct | gaagccgcgc | 480 |
| atgcgcaaga | tcttcagccg | gctcatctac | atcgcgcagt | ccaaaggtgc | ttggattctc | 540 |
| acgggaggca | cccattatgg | cctgatgaag | tacatcgggg | aggtggtgag | agataacacc | 600 |
| atcagcagga | gttcagagga | gaatattgtg | gccattggca | tagcagcttg | ggcatggtc | 660 |
| tccaaccggg | acaccctcat | caggaattgc | gatgctgagg | gctattttt | agcccagtac | 720 |
| cttatggatg | acttcacaag | agatccactg | tatatcctgg | acaacaacca | cacacatttg | 780 |
| ctgctcgtgg | acaatggctg | tcatggacat | cccactgtcg | aagcaaagct | ccggaatcag | 840 |
| ctagagaagt | atatctctga | gcgcactatt | caagattcca | actatggtgg | caagatcccc | 900 |
| attgtgtgtt | ttgcccaagg | aggtggaaaa | gagactttga | aagccatcaa | tacctccatc | 960 |
| aaaaataaaa | ttccttgtgt | ggtggtggaa | ggctcgggcc | agatcgctga | tgtgatcgct | 1020 |
| agcctggtgg | aggtggagga | tgccctgaca | tcttctgccg | tcaaggagaa | gctggtgcgc | 1080 |
| tttttacccc | gcacggtgtc | ccggctgcct | gaggaggaga | ctgagagttg | gatcaaatgg | 1140 |
| ctcaaagaaa | ttctcgaatg | ttctcaccta | ttaacagtta | ttaaaatgga | agaagctggg | 1200 |
| gatgaaattg | tgagcaatgc | catctcctac | gctctataca | aagccttcag | caccagtgag | 1260 |
| caagacaagg | ataactggaa | tgggcagctg | aagcttctgc | tggagtggaa | ccagctggac | 1320 |
| ttagccaatg | atgagatttt | caccaatgac | cgccgatggg | agtctgctga | ccttcaagaa | 1380 |
| gtcatgttta | cggctctcat | aaaggacaga | cccaagtttg | tccgcctctt | tctggagaat | 1440 |
| ggcttgaacc | cacggaagtt | tctcacccat | gatgtcctca | ctgaactctt | ctccaaccac | 1500 |
| ttcagcacgc | ttgtgtaccg | gaatctgcag | atcgccaaga | attcctataa | tgatgccctc | 1560 |
| ctcacgtttg | tctggaaact | ggttgcgaac | ttccgaagag | gcttccggaa | ggaagacaga | 1620 |
| aatgccggg | acgagatgga | catagaactc | acgacgtgt | ctcctattac | tcggcacccc | 1680 |
| ctgcaagctc | tcttcatctg | ggccattctt | cagaataaga | aggaactctc | caaagtcatt | 1740 |
| tgggagcaga | ccaggggctg | cactctggca | gccctgggag | ccagcaagct | tctgaagact | 1800 |
| ctggccaaag | tgaagaacga | catcaatgct | gctggggagt | ccgaggagct | ggctaatgag | 1860 |
| tacgagaccc | gggctgttga | gctgttcact | gagtgttaca | gcagcgatga | agacttggca | 1920 |
| gaacagctgc | tggtctattc | ctgtgaagct | tggggtggaa | gcaactgtct | ggagctggcg | 1980 |
| gtggaggcca | cagaccagca | tttcatcgcc | cagcctgggg | tccagaattt | tctttctaag | 2040 |
| caatggtatg | gagagatttc | ccgagacacc | aagaactgga | agattatcct | gtgtctgttt | 2100 |

-continued

```
attatacccct tggtgggctg tggctttgta tcatttagga agaaacctgt cgacaagcac    2160
aagaagctgc tttggtacta tgtggcgttc ttcacctccc ccttcgtggt cttctcctgg    2220
aatgtggtct tctacatcgc cttcctcctg ctgtttgcct acgtgctgct catggatttc    2280
cattcggtgc cacaccccccc cgagctggtc ctgtactcgc tggtctttgt cctcttctgt    2340
gatgaagtga cacagtggta cgtaaatggg gtgaattatt ttactgacct gtggaatgtg    2400
atggacacgc tggggctttt ttacttcata gcaggaatng tatttcggct ccactcttct    2460
aataaaagct ctttgtattc tggacgagtc attttctgtc tggactacat tattttcact    2520
ctaagattga tccacatttt tactgtaagc agaaacttag acccaagat tataatgctg    2580 cagaggatgc tgatcgatgt gttcttcttc ctgttcctct ttgcggtgtg gatggtggnc    2640
tttggcgtgg ccaggcaagg gatccttagg cagaatgagc agcgctggag gtggatattc    2700
cgttcggtca tctacgagcc ctacctggcc atgttcggcc aggtgcccag tgacgtggat    2760
ggtaccacgt atgactttgc ccactgcacc ttcactggga atgagtccaa gccactgtgt    2820
gtggagcngg atgagcacaa nctgccccgg ttccccgagt ggatcaccat cccctggtg    2880 tgcatctaca tgttatccac caacatcctg ctggtcaacc tgctggtcgc catgtttggc    2940
tacacggtgg gcaccgtcca ggagaacaat gaccaggtct ggaagttcca gaggtacttc    3000
ctggtgcagg agnactgcag ccgcctcaat atccccttcc ccttcatcgt cttcgcttac    3060
ttctacatgg tggtgaagaa gtgcttcaag tgttgctgca aggagaaaaa catggagtct    3120
tctgtctgct gtttcaaaaa tgaagacaat gagactctgg catgggaggg tgtnatgaag    3180
gaaaactacc ttgtcaagat caacacaaaa gccaacgaca cctcagagga aatgaggcat    3240
cgatttagac aactggatnc aaagcttaat gatctcaagg gtcttctgaa agagattgct    3300
aataaaatca aataa                                                     3315
```

<210> SEQ ID NO 5  
<211> LENGTH: 200  
<212> TYPE: PRT  
<213> ORGANISM: Artificial Sequence  
<220> FEATURE:  
<223> OTHER INFORMATION: Description of Artificial Sequence:poly Gly flexible linker  
<220> FEATURE:  
<221> NAME/KEY: VARIANT  
<222> LOCATION: (6)...(200)  
<223> OTHER INFORMATION: Xaa = Gly or absent

<400> SEQUENCE: 5

```
Gly Gly Gly Gly Gly Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125
```

```
Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa
        195                 200
```

METHODS OF MODULATING COLD SENSORY PERCEPTION VIA A COLD- AND MENTHOL-SENSITIVE RECEPTOR (CMR1)

CROSS REFERENCE TO RELATED APPLICATIONS

This application is a continuation application of U.S. application Ser. No. 13/340,443, filed Dec. 29, 2011, now U.S. Pat. No. 8,470,545, which is a divisional application of U.S. Ser. No. 12/905,001, filed Oct. 14, 2010, now U.S. Pat. No. 8,361,733, which is a divisional application of U.S. Ser. No. 12/032,485, now U.S. Pat. No. 7,838,253, filed Feb. 15, 2008, which is a divisional application of U.S. Ser. No. 10/352,724, now U.S. Pat. No. 7,371,841, filed Jan. 27, 2003, which claims priority to U.S. Ser. No. 60/351,974, filed Jan. 25, 2002, and U.S. Ser. No. 60/355,037, filed Feb. 7, 2002, which are herein incorporated by reference in their entireties.

STATEMENT AS TO RIGHTS TO INVENTIONS MADE UNDER FEDERALLY SPONSORED RESEARCH AND DEVELOPMENT

This invention was made with government support under grant number GM44298 awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The sequence listing written file -1232-7.TXT, created on Jun. 26, 2013, 32,768 bytes, machine format IBM-PC, MS-Windows operating system, is hereby incorporated by reference in its entirety for all purpose.

REFERENCE TO A SEQUENCE LISTING

This application includes a Sequence Listing as a text file named "-1232-6.txt" created Dec. 29, 2011 and containing 29,778 bytes. The material contained in this text file is incorporated by reference in its entirety for all purposes.

FIELD OF THE INVENTION

The current invention relates to regulation of cold sensation. More particularly, the present invention is directed to nucleic acids encoding a member of the transient receptor potential (TRP) ion channel family, cold- and menthol-sensitive receptor (CMR1), which is involved in detecting cold stimuli. The invention further relates to methods for identifying and using agents, including small organic molecules, antibodies, peptides, nucleic acids, antisense nucleic acids, and ribozymes, that modulate cold sensation via modulation of CMR1; as well as to the use of expression profiles and compositions in diagnosis and therapy related to cold sensation.

BACKGROUND OF THE INVENTION

The somatosensory system can detect changes in ambient temperature over a remarkably wide range, enabling us to discriminate among thermal stimuli of an innocuous (cool or warm) or noxious (cold or heat) quality. This process is initiated when a thermal stimulus excites the peripheral terminals of primary sensory neurons from dorsal root or trigeminal ganglia, which innervate regions of the trunk and head, respectively. These neurons convert thermal stimuli into electrochemical signals (i.e. action potentials) and relay information to integrative centers in the spinal cord and brain (Fields, *Pain* (1987); Julius & Basbaum, *Nature* 413:203-10 (2001)). Noxious (painful) heat is detected by primary sensory neurons that respond with a moderate thermal threshold of ~43° C. or with a high threshold of ~52° C. (Raja et al., in *Textbook of Pain*, pages 11-57 (Wall & Melzack, eds., 1999); Nagy & Rang, *Neuroscience* 88:995-7 (1999)). Insights into the molecular mechanisms of heat sensation have come from the cloning and characterization of the vanilloid receptor (VR1), an excitatory ion channel on sensory neurons that is activated by capsaicin, the main pungent ingredient in "hot" chili peppers and is also activated by noxious heat at temperatures >43° C. (Caterina et al., *Nature* 389:816-24 (1997)). Indeed, electrophysiological, anatomical, and genetic studies support this hypothesis and show that VR1 is essential for the development of thermal hypersensitivity following tissue injury (Caterina & Julius, *Annu. Rev. Neurosci.* 24:487-517 (2001)). A related ion channel, VRL-1, does not respond to capsaicin, but is activated by temperatures >50° C., suggesting that it contributes to heat sensitivity of high threshold neurons (Caterina et al., *Nature* 398:436-41 (1999)). Both VR1 and VRL-1 belong to the transient receptor potential (TRP) ion channel family.

In contrast to the understanding of noxious heat sensation, little is known about how we detect cold. Recordings from cutaneous sensory nerves in the cat suggest that noxious cold (<15° C.) is detected primarily by two classes of unmyelinated C-fibers: those that also respond to high-threshold (noxious) mechanical and heat stimuli, and another population that is activated by low-threshold (innocuous) mechanical stimuli. Another class of C-fibers can be activated by moderate cooling of the skin to 25° C., but are mechanically insensitive (Bessou & Perl, *J. Neurophysiol.* 32:1025-43 (1969)). Interestingly, some fibers in this latter class are also activated at temperatures >43° C., a phenomenon classically described as a paradoxical response of cold fibers to noxious heat (Campero et al., *J. Physiol.* 535:855-65 (2001); Dodt & Zotterman, *Acta Physiol. Scand.* 26:358-365 (1952)). Studies in rodents show that unmyelinated C-fibers as well as thinly myelinated M fibers are sensitive to noxious cold, but the percentage of such units responding to cold ranges from ~10% to 100%, depending on the stimulus intensity and species examined (Kress et al., *J. Neurophysiol.* 68:581-95 (1992); Caterina et al., *Science* 288:306-13 (2000); Simone & Kajander, *Neurosci. Lett.* 213:53-6 (1996); Simone & Kajander, *J. Neurophysiol.* 77:2049-60 (1997); Cain et al., *J. Neurophysiol.* 85:1561-74 (2001)).

This wide variability in the literature may reflect the fact that thermal thresholds for cold-sensitive fibers are not as well defined as they are for heat-sensitive units. Moreover, psychophysical thresholds for cold-evoked pain are not as precise as they are for heat and thus fiber types that transduce sensations of innocuous cool or noxious cold are not as firmly established. At the cellular level, calcium-imaging and patch-clamp studies of dissociated dorsal root ganglion (DRG) neurons have shown that cold (~20° C.) promotes calcium influx, possibly through the direct opening of calcium-permeable ion channels on these cells (Reid & Flonta, *Nature* 413:480 (2001); Suto & Gotoh, *Neuroscience* 92:1131-5 (1999)). However, several other mechanisms have been proposed to explain cold-evoked membrane depolarization, including inhibition of background $K^+$ channels (Reid & Flonta, *Neurosci. Lett.* 297:171-4 (20010), activation of $Na^+$-selective degenerin channels (Askwith et al., *Proc. Natl. Acad. Sci.*

U.S.A. 98:6459-63 (2001)), inhibition of (Na$^+$/K$^+$) ATPases (Pierau et al., *Brain Res.* 73:156-60 (1974)), or differential effects of cold on voltage-gated Na$^+$ and K$^+$ conductances (Braun et al., *Pflugers Arch.* 386:1-9 (1980)). Thus it is not clear whether cold excites sensory neurons by activating a discrete "cold receptor," or by modulating a constellation of excitatory and inhibitory channels on these cells.

Fifty years ago, Hensel & Zotterman (*Acta Physiol. Scand.* 24:27-34 (1951)) showed that menthol potentiates responses of trigeminal fibers to cold by shifting their thermal activation thresholds to warmer temperatures. Moreover, they proposed that cooling compounds mediate their psychophysical effects by interacting with a protein in sensory neurons that is specific to the process of cold transduction. Although recent studies of sensory nerve fibers or dissociated DRG neurons in culture support this idea, no unifying cellular mechanism has been proposed to explain menthol's action. For example, one model proposes that menthol inhibits voltage-dependent Ca$^{2+}$ channels (Swandulla et al., *Pflugers Arch.* 409:52-9 (1987)), thereby decreasing activation of Ca$^{2+}$-dependent K$^+$ channels and prolonging depolarization of cold-sensitive fibers (Schafer et al., *J Gen Physiol.* 88:757-76 (1986)). Another model predicts that menthol directly activates calcium-permeable ion channels on these cells (Reid & Flonta, *Nature* 413:480 (2001); Okazawa et al., *Neuroreport* 11: 2151-5 (2000)). In any case, there is currently no direct pharmacological or biochemical evidence to support the existence of a bona fide menthol binding site on sensory neurons, nor is it clear whether menthol and cold act through the same molecular entity to depolarize these cells.

Cold/menthol receptor gene and related genes have been reported in the literature under various different names. For example, McKemy et al., *Nature* 416:52-58 (2002) refer to this gene as CMR1 and suggest the role of this gene as a cold receptor and also suggest a possible general rule for TRP channels in thermosensation. Also, Peier et al. (*Cell* 108(5): 705-715 (2002) and *Science* 296:2046-9 (2002)) refer to a TRP channel that they name to TRPM8, which is reported to be a distant relative of VR1, that is activated by cold temperatures and by a cooling agent, menthol. Additionally, Tsavaler et al. and others of Dendreon Corporation refer to a gene related to CMR1 by the names Trp-8 and SP 1-4, and teach that this gene is upregulated in prostate cancer and other malignancies.

The current invention is based on the discovery that the molecular site of menthol action is an excitatory ion channel expressed by small-diameter neurons in trigeminal and dorsal root ganglia. Remarkably, the cloned channel is also activated by cold (8 to 28° C.), demonstrating that menthol does, indeed, elicit a sensation of cool by serving as a chemical agonist of a thermally responsive receptor. This cold- and menthol-sensitive receptor (CMR1) exhibits the highest similarity to members of the so-called long TRP or TRPM channel subfamily, making it a close molecular cousin of the heat-activated channels, VR1 and VRL-1. Thus, TRP channels are the primary molecular tranducers of thermal stimuli and pain related to thermal stimuli within the mammalian somatosensory system.

SUMMARY OF THE INVENTION

The present invention therefore provides nucleic acids encoding a cold- and menthol-sensitive receptor, CMR1, including variants and chimeras thereof. The invention further provides methods of using CMR1 polynucleotide and polypeptide sequence to screen for compounds, including small organic molecules, antibodies, peptides, lipids, nucleic acids, antisense molecules, siRNA molecules, and ribozymes, to modulate cold/cool sensation. Such compounds can be used as flavoring or perfume agents or as components of medicaments to provide a cool or cold sensation. Additionally, compounds that modulate CMR1 activity may be used to modulate pain perception, e.g., in the treatment of pain and for the treatment of pain induced by cool or cold and/or menthol stimulus.

In one aspect of the invention, nucleic acids encoding CMR1 protein, are provided. In another aspect, the present invention provides nucleic acids, such as probes, antisense oligonucleotides, and ribozymes, that hybridize to a gene encoding a CMR1 protein, e.g., a nucleic acid sequence set out in SEQ ID NO:2 or 4. Often, the nucleic acid encodes a protein comprising at least about 95% or 98% identity of an amino acid sequence set out in SEQ ID NO:1 or 3. Often, the nucleic acid is a sequence comprising at least about 95% or 98% identity of an amino acid sequence set out in SEQ ID NO:2 or 4. In another aspect, the invention provides expression vectors and host cells comprising CMR1-encoding nucleic acids. In another aspect, the present invention provides CMR1 proteins and antibodies thereto. The CMR1 protein can be fused to a heterologous protein, i.e., to make a fusion protein.

Often, the CMR1 polypeptide, variant, chimera, or fragment thereof, is recombinant and the cell that expressed the CMR1 polypeptide, variant, chimera, or fragment thereof is a non-neuronal cell. In some embodiments, the host cell is from a mammalian cell line, e.g., a 293 or a CHO cell line.

In another aspect, the invention provides a method for identifying a compound that modulates cold/cool sensation or pain, the method comprising the steps of: (i) contacting a cell comprising a CMR1 polypeptide, variant, chimera, or fragment thereof, with the compound, wherein the CMR1 polypeptide, variant, chimera, or fragment thereof is encoded by a nucleic acid that hybridizes under stringent conditions to a nucleic acid comprising a CMR1 nucleotide sequence of SEQ ID NO:2 or 4, and forms a cation channel; and (ii) determining the chemical or phenotypic effect of the compound upon the cell comprising the CMR1 polypeptide, thereby identifying a compound that modulates cold sensation or pain.

In another aspect, the present invention provides a method for identifying a compound that modulates cold sensation or pain, the method comprising the steps of: (i) contacting the compound with a CMR1 polypeptide, variant, chimera, or fragment thereof, the CMR1 polypeptide, variant, chimera, or fragment thereof is encoded by a nucleic acid that hybridizes under stringent conditions to a nucleic acid comprising a CMR1 nucleotide sequence; (ii) determining the physical effect of the compound upon the CMR1 polypeptide; and (iii) determining the chemical or phenotypic effect of the compound upon a cell comprising an CMR1 polypeptide or fragment thereof, thereby identifying a compound that modulates cold sensation or pain.

In one embodiment, the CMR1 polypeptide or fragment thereof is encoded by a nucleic acid that hybridizes under stringent conditions to a nucleic acid comprising a sequence of SEQ ID NO:2 or 4. Often, the nucleic acid encodes a CMR1 polypeptide comprising at least about 85%, 95%, or 98% identity to an amino acid sequence set out in SEQ ID NO:1 or 3. Often, the nucleic acid comprises at least about 85%, 95%, or 98% identity to a nucleic acid sequence set out in SEQ ID NO:2 or 4.

In another embodiment, the nucleic acid encodes a CMR1 polypeptide that has at least 60% identity to an amino acid sequence set out in SEQ ID NO:1 or 3.

In a further embodiment, the method comprises contacting the compound with a CMR1 polypeptide or fragment thereof is encoded by a nucleic acid that hybridizes under moderately stringent conditions to a nucleic acid comprising a sequence of SEQ ID NO:2 or 4. Often, the nucleic acid has at least 60% identity to a nucleic acid sequence set out in SEQ ID NO:2 or 4.

In one embodiment, the chemical or phenotypic effect is determined by measuring CMR1 expression, intracellular $Ca^{2+}$ mobilization, or changes in membrane currents.

In another embodiment, the CMR1 polypeptide is encoded by a nucleic acid comprising a sequence set forth in SEQ ID NO:2 or 4. In another embodiment, the CMR1 polypeptide comprises an amino acid sequence of SEQ ID NO:1 or 3.

In one aspect, the present invention provides a method of modulating cold sensation or pain in a subject, the method comprising the step of administering to the subject a therapeutically effective amount of a compound identified using the methods described above. The compound can be administered using a variety of routes and formulations (see, e.g., Remington's Pharmaceutical Sciences, 17th ed., 1989)

In one embodiment, the subject is a human.

In one embodiment, the present invention provides method of modulating cold sensation or pain in a subject, the method comprising the step of administering to the subject a therapeutically effective amount of an CMR1 polypeptide, the polypeptide encoded by a nucleic acid that hybridizes under stringent conditions to a nucleic acid comprising a CMR1 nucleotide sequence.

In another aspect, the present invention provides a method of modulating cold sensation or pain in a subject, the method comprising the step of administering to the subject a therapeutically effective amount of a nucleic acid encoding a CMR1 polypeptide or fragment thereof, wherein the nucleic acid hybridizes under stringent conditions to a nucleic acid encoding a polypeptide comprising a CMR1 nucleotide sequence.

In another aspect, the invention provides a compound capable of modulating a cold receptor identified using the methods disclosed herein.

BRIEF DESCRIPTION OF THE DRAWINGS

FIG. 1A-F. A subset of trigeminal neurons express an inwardly rectifying Ca 2+-permeable channel activated by menthol and cold. A, Responses of dissociated trigeminal neurons to cold (7° C.), menthol (500 μM), and capsaicin (1 μM) were assessed by calcium imaging. Arrowheads mark menthol responding cells that were insensitive to capsaicin. Relative calcium concentrations are indicated by Fura-2 ratio. The percentage (±s.e.m.) of excitable (potassium-sensitive) cells responding to each stimulus is indicated below. B, Electrophysiological responses of trigeminal neurons to menthol (50 μM), cyclohexanol (100 mM), menthone (100 μM), or cold (16° C.) were measured in both inward and outward directions ($V_{hold}$=−60 and +80 mV, respectively). Increasing temperature of perfusate (from RT to 30° C.) completely antagonized currents evoked by 100 μM menthol (right). Perfusate temperatures are indicated below each current trace. C, Menthol (50 μM, gray)- and cold (16°, black)- evoked responses show strong outward rectification. Changing the pipette solution to Cs-gluconate did not shift the reversal potential significantly (not shown). Time dependence of menthol-evoked whole-cell currents was analyzed using 400 ms voltage ramps ranging from −120 to +70 mV in 10 mV steps. Inset shows baseline currents (black) and menthol-evoked responses (gray) in nominally $Ca^{2+}$ free bath solution at RT using a CsCl-filled recording electrode. D, Voltage ramps (−120 to +80 mV in 200 ms) were used to establish current-voltage relationships in different extracellular solutions. Recording electrodes were filled with standard pipette solution. Replacement of extracellular NaCl (140 mM) with equimolar KCl or NMDG shifted the reversal potential from $E_{rev(Na)}$=−5.11±3.11 mV (n=6) to $E_{rev(K)}$=−4.45±2.01 mV (n=3) and $E_{rev(NMDG)}$=−84.99±11.51 mV (n=7). Replacement of extracellular NaCl with 125 mM NMDG and 10 mM $CaCl_2$ shifted the reversal to $E_{rev(CaNMDG)}$=−43.28±4.59 mV (n=6, $P_{Ca}/P_{Na}$=3.22). Change of pipette solution from standard (140 KCl, 5 CsCl) to 140 CsCl in nominally Ca 2+ free bath solution shifted the reversal from 0.50±0.64 mV (n=5) to −3.56±1.90 mV (n=6, not shown). E, Concentration-response curve for menthol-evoked inward currents (Vhold=−60 mV) in trigeminal neurons. Membrane currents in each neuron were normalized to 1 mM menthol at room temperature. Each point represents mean value (±s.e.m.) from six independent neurons. Data were fit to the Hill equation. F, Temperature-response curves (from 33° C. to 16° C.) were determined for trigeminal neurons in the presence (gray) or absence (black) of 10 μM menthol. Menthol potentiated the size of cold-evoked currents and shifted thermal thresholds from 27.1±0.5° C. to 29.6±0.3° C. (n=4).

FIG. 3A-E. Electrophysiological properties of menthol-induced currents in transfected HEK293 cells. A, Time dependence of menthol induced whole-cell currents were analyzed using 400 ms voltage step pulses ranging from −120 to +70 mV in 10 mV steps (top). Traces show current response induced by menthol (50 μM) at RT in nominally Ca 2+ free bath solution using a CsCl-filled recording electrode. Current-voltage relationship (bottom) was obtained from the same pulse protocol using 200 μM menthol (RT) by plotting the time-independent current component as a function of membrane voltage. Menthol currents reversed at −4.49±1.07 mV (±s.e.m., n=4) and show strong outward rectification. A similar current-voltage relationship was obtained for 2 μM icilin from a 200 ms voltage ramp (−120 to +80 mV). B, 200 ms voltage ramps ranging from −120 to +80 mV were used to record current-voltage curves in different extracellular solutions. Recording electrodes were filled with standard pipette solution. Replacement of extracellular NaCl (140 mM) with equimolar KCl or NMDG shifted the reversal potential from $E_{rev(Na)}$=−3.79±2.36 mV (n=13) to $E_{rev(K)}$=0.82±1.02 mV (n=8) and $E_{rev(NMDG)}$=−77.22±5.90 mV (n=11), respectively ($P_K/P_{Na}$=1.20, $P_{NMDG}/P_{Na}$=0.06). Replacement of extracellular NaCl with 125 mM NMDG and 10 mM $CaCl_2$ shifted the reversal to $E_{rev(CaNMDG)}$=−35.16±8.00 mV (n=9; PCa/PNa=3.34). Change of pipette solution from standard (140 KCl, 5 CsCl) to 140 CsCl in nom. $Ca^{2+}$ free bath solution shifted the reversal from −2.27±1.02 mV (n=3) to −4.49±1.07 mV (n=4, $P_{Cs}/P_K$=1.14, not shown). C, Responses evoked by consecutive menthol applications (50 mM, standard pipette solution) are characterized by a decrease of 53.9±1.7% (n=3)

Figure 2A:
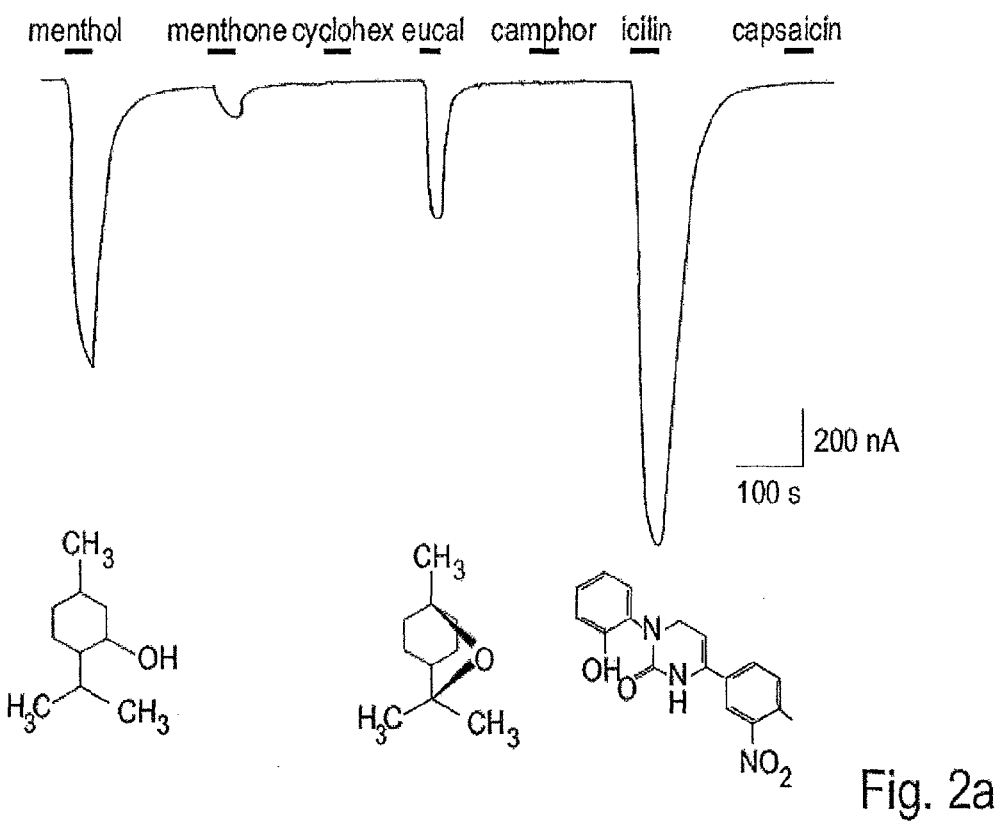
FIG. 2A-B. Cooling compounds activate the cloned receptor. A, An oocyte expressing the cloned receptor was exposed to consecutive applications of menthol (100 μM), menthone (500 μM), cyclohexanol (500 μM), eucalyptol (20 mM), camphor (1 mM), icilin (300 nM), and capsaicin (1 μM). Resulting membrane currents were measured under voltage clamp at −60 mV. Bars denote the duration of agonist application. Chemical structures for menthol, eucalyptol, and icilin are shown below their respective responses. B, Concentration-response curves for icilin (boxes), menthol (circles), and eucalyptol (triangles). Responses were normalized to those evoked by 500 μM menthol. Each point represents mean values (±s.e.m.) from 4 to 9 independent oocytes.
Figure 2B:
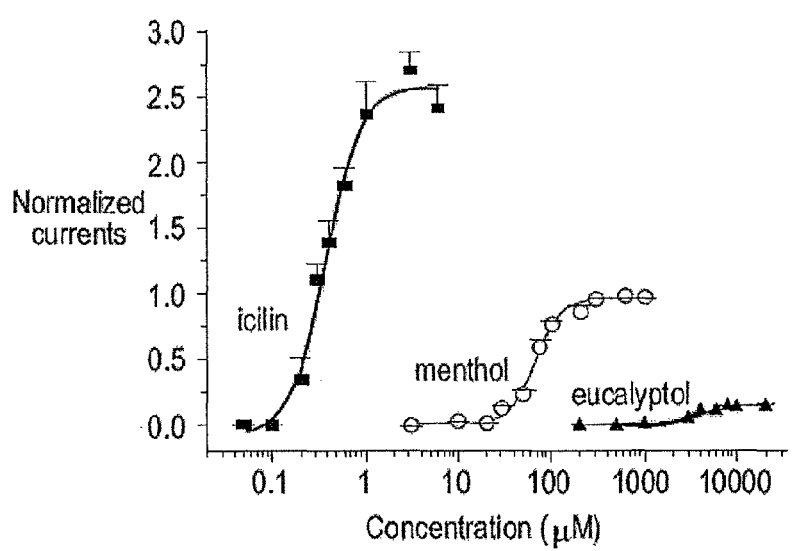

in peak current level between first and second application in the presence of 2.5 mM extracellular Ca 2+ (black bars) and 9.1±7.0% in nominally Ca 2+ free (gray bar) bath solution (t-test; p=0.03; n=3). Icilin-evoked currents depend on extracellular Ca 2+ and desensitized by 78.8±17% (n=3) 20 s after application (relative to peak currents). D, Single channel traces were recorded from transfected HEK293 cells in the cell-attached patch configuration at different holding potentials (in NaCl buffer with the addition of 0.1 mM EGTA and 5 mM menthol in the pipette). E, Single channel current amplitude was obtained by measuring mean current amplitudes at various positive holding potentials, as shown. Slope conductance was obtained by linear regression fit, yielding a single channel conductance of 83±3 pS (n=3).

FIG. 4A-F. The menthol receptor is cold sensitive. A, Inward currents (top) were evoked in the same menthol receptor-expressing oocyte by repetitive decreases in perfusate temperature. Cooling ramps (bottom) were applied at two different rates (0.2° C./s; 1° C./s). B, Temperature-response profile of the cold-evoked currents shown in panel (A). C, Response profiles of cold-evoked currents in seven independent oocytes in the absence (black lines) or presence of a sub-activating concentration of menthol (20 µM, gray lines). D, Inward currents evoked in a menthol receptor-expressing oocyte by a saturating cold stimulus (35 to 5° C.) were smaller than those evoked by a maximal dose of room temperature menthol (500 µM). E, Current-voltage relationship for a cold (14° C.)-evoked stimulus in menthol receptor-transfected cells in the absence or presence of sub-activating dose (10 µM) of menthol. Menthol induced potentiation and outward rectification of cold-evoked currents are also evident in the accompanying current traces (above) obtained at various voltage steps (−120 to 70 mV). F, Current-voltage relationship in transfected HEK293 cells for basal current at 22° before and after warming to 31° C.

FIG. 5A-B. CMR1 is a member of the TRP family of ion channels. A, The predicted amino acid sequence (SEQ ID NO:1) determined from the CMR1 cDNA. Open boxes designate predicted transmembrane domains and amino acids encompassing the conserved TRP family motif is underlined. B, Schematic comparison of CMR1 with other TRPM family members, TRPM2 and TRPM7. Proteins are aligned using putative transmembrane domains and TRP motif as landmarks. Numeric label is based on the TRPM7 sequence. CMR1 has a significantly shorter C-terminal tail and does not contain any conserved domains indicative of enzymatic activity associated with TRPM2 (ADP ribose pyrophosphatase, Nudix motif) or TRPM7 (protein kinase).

FIG. 6A-B. CMR1 is expressed by small-diameter neurons in trigeminal and dorsal root ganglia. A, Poly A+RNA from adult rat trigeminal ganglia (TG), dorsal root ganglia (DRG), spinal cord (SC) and brain were analyzed by Northern blotting, revealing two predominant transcripts of ~6 and 5 kb. The blot was re-probed with a rat cyclophilin cDNA (bottom) to control for sample loading. B, Histological sections from adult rat trigeminal or dorsal root ganglia showed selective staining (brown) with a digoxygenin-labeled CMR1 probe over neurons with small-diameter (~19 micron) cell bodies (scale bar=50 micron).

Figure 7A:
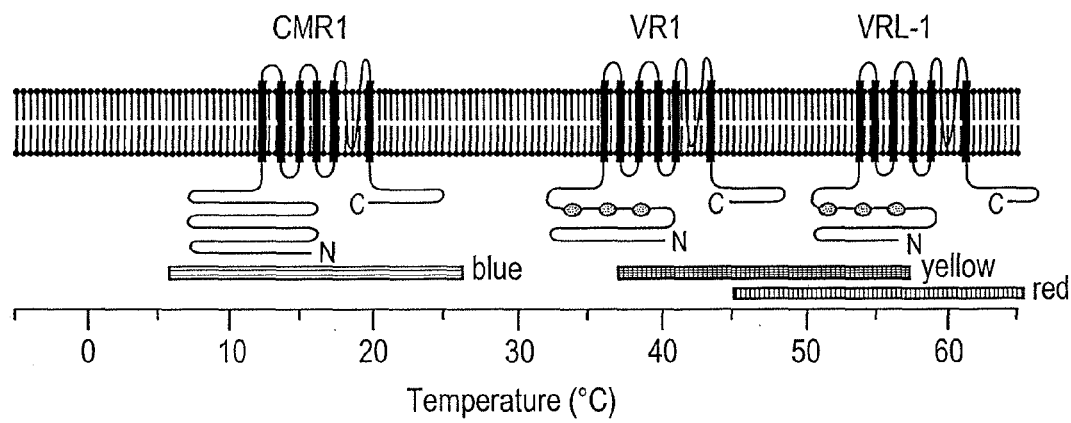
Figure 7B:
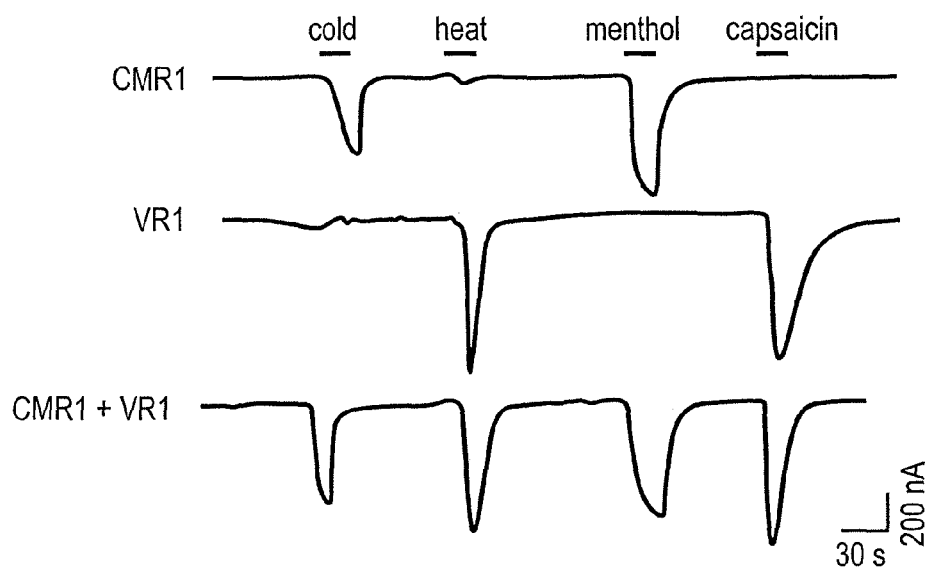

FIG. 7A-B. TRP-like channels mediate thermosensation from cold to hot. a, Schematic representation of the thermal sensitivity ranges of CMR1, VR1, and VRL-1. Based on a combination of in vitro and in vivo analyses, these channels can theoretically account for thermosensation over a wide range of ambient temperatures. The ranges of each proteins' temperature sensitivity are denoted by bars. Other molecules may contribute to temperature sensation in zones not necessarily covered by these channels, in particular those of a warm (30 to 40° C.) or extremely cold (<5° C.) nature. B, Oocytes co-expressing CMR1 and VR1 demonstrate that these channels are sufficient to confer thermal responsiveness to both cold (menthol) and heat (capsaicin) independently. Bars above traces indicate application of thermal or chemical stimuli (cold, 35 to 8° C.; heat, 25 to 50° C.; menthol, 100 µM; capsaicin, 1 µM).

DETAILED DESCRIPTION OF THE INVENTION

Introduction

For the first time, a protein from the TRP family of channel proteins, CMR1, has been functionally identified as a protein involved in regulating cold/menthol sensation. The present invention, therefore, has functionally identified CMR1 as a drug target for compounds that regulate the cold sensation or pain sensation, particularly pain that is stimulated by cold. Such compounds can be used in various processes that involve cold perception, for example, as flavor or perfume ingredients or as ingredients in medicinal preparations.

In some applications, the compounds may be used to elicit an effect on breathing or thirst. It has been noted that cold air blown over the mouth inhibits respiration, and that menthol compounds, which create a sensation of airway cooling, also decrease the activity of upper respiratory tract muscles (Eccles, *J. Pharm. Pharmacol.* 46:618-30, 1994). Accordingly, CMR1 agonists could be used as a cooling agent in preparations such as lozenges, or medications, to provide a decrease in respiratory rate, e.g., to reduce anxiety. Menthol has also been reported to decrease the thirst response. Similarly, CMR1 modulators identified using the methods described herein could also be included in beverages, food, or medications to decrease the thirst response.

CMR1 modulators may also be used to modulate disorders associated with cold perception, such as pain. Additionally compounds that modulate CMR1 activity could also be used as inhibitors of cancer cell proliferation. Expression or repression of several TRP channel genes in tumor cells also suggest that these proteins have effects on cell proliferation, for example, through their ability to regulate intracellular calcium levels. Among normal tissues examined, human TRPM8, which is 92% identical to the CMR1 protein sequence set forth in SEQ ID NO:1, was found to be expressed in prostate epithelia, as well as exhibiting increased expression in a variety of tumors, including prostate, melanoma, colorectal, and breast carcinoma (Tsavaler et al., *Cancer Res.* 61:3760-9 (2001)). This suggests that CMR1 may function as an oncogene or tumor promoter and that compounds that modulate CMR1 and intracellular calcium levels may be useful as agents to inhibit cancer cell proliferation.

CMR1 proteins may also be used as biosensors, i.e., molecular thermometers.

The present invention provides isolated nucleic acid and amino acid sequences encoding CMR1 and methods of production of CMR1. Structurally, the CMR1 cDNA includes an open reading frame of 3312 bp (SEQ ID NO:2) that encodes a polypeptide of 1104 amino acids in length (SEQ ID NO:1). The amino acid sequence can be aligned with a 92% sequence identity with the human amino acid sequence of the transient receptor potential (TRP) ion channel family, TRPM8 (or trp-p8) (see, e.g., Tsavaler et al., *Cancer Res.* 61:3760-3769, 2001; U.S. Pat. No. 6,194,152, and WO 99/09166).

CMR1 proteins form channels that have cation channel activity; in particular they exhibit calcium permeability. The protein has relatively high permeability to calcium and little selectivity among monovalent cations. Channel activity can be effectively measured, e.g., by recording ligand-induced changes in [$Ca^{2+}$]$_i$ and measuring calcium influx using fluorescent $Ca^{2+}$-indicator dyes and fluorometric imaging.

CMR1 is expressed in a number of tissues, including sensory neurons, as well as prostate epithelia and a variety of tumors, e.g., other epithelial tumors. Additional tissues that may express CMR1 or homologues include the brain and regions of the brain, such as the hypothalamus, that regulate core body temperature.

Within the TRP family, TRPM2 and TRPM7 have been electrophysiologically characterized and shown to behave as bifunctional proteins in which enzymatic activities associated with their long C-terminal domains are believed to regulate channel opening. Specifically, TRPM2 contains a Nudix motif associated with adenosine-5'-diphosphoribose (ADPR) pyrophosphatase activity and is gated by cytoplasmic ADPR and nicotinamide adenine dinucleotide (NAD) (Perraud et al., *Nature* 411:595-9 (2001); Sano et al., *Science* 293:1327-30 (2001)). TRPM7 contains a protein kinase domain that is required for channel activation (Runnels et al., *Science* 291: 1043-7 (2001)). In contrast, CMR1 has a significantly shorter C-terminal region (FIG. 5*b*) and does not contain any known enzymatic domains that might be associated with channel regulation.

CMR1 encodes a channel protein that is sensitive to temperatures that encompass all of the innocuous cool (e.g., 15 to 28° C.) and part of the noxious cold (e.g., 8 to 15° C.) range. Furthermore, CMR1 could contribute to depolarization of fibers at temperatures in the ultra-cold range (below 8° C.), for example, if the channel is modified or modulated in a manner that extends its sensitivity range in vivo. Indeed, VR1 and several other members of the TRP channel family are regulated by receptors that couple to phospholipase C (PLC). In particular, the thermal activation threshold for VR1 can be markedly shifted to lower temperatures by inflammatory agents that either activate PLC signaling systems (e.g. bradykinin and nerve growth factor) or modulate the channel directly (e.g. protons and lipids) (Caterina & Julius, *Annu. Rev. Neurosci.* 24:487-517 (2001); Chuang et al., *Nature* 411: 957-62 (2001)).

When expressed together, CMR1 and VR1 could endow a cell with distinct thermal thresholds and temperature response ranges for cold and hot, respectively (FIG. 7*b*). Indeed, calcium imaging data suggests that a significant proportion (~50%) of CMR1-expressing small-diameter neurons also express VR1 and can therefore be categorized as cold and heat-responsive nociceptors. These observations provide a molecular explanation for the paradoxical activation of low-threshold thermoreceptors by noxious heat (Campero et al., *J. Physiol.* 535:855-65 (2001); Dodt & Zotterman, *Acta Physiol. Scand.* 26:358-365 (1952)) or for the fact that noxious cold is sometimes perceived as burning pain (Craig & Bushnell, *Science* 265:252-5 (1994)). The cloning of CMR1 now makes it possible to assess the contribution of this channel and CMR1-expressing sensory neurons to the detection of cool and cold stimuli in vivo using histological, electrophysiological, and genetic methods.

When applied to skin or mucous membranes, menthol produces a cooling sensation, inhibits respiratory reflexes and, at high doses, elicits a pungent or irritant effect that is accompanied by local vasodilation (Eccles, *J. Pharm. Pharmacol.* 46:618-30 (1994); Eccles, *Appetite* 34:29-35 (2000)). Most, if not all, of these physiological actions can be explained by excitation of sensory nerve endings within these tissues, but CMR1 receptors elsewhere may also contribute to these or other effects of cooling compounds or cold stimuli.

The invention also provides methods of screening for modulators, e.g., activators, inhibitors, stimulators, enhancers, etc., of CMR1 nucleic acids and proteins, using the sequences provided herein as well as variants, and orthologs, e.g., human orthologs, thereof. Such modulators can affect CMR1 activity, e.g., by modulating CMR1 transcription, translation, mRNA or protein stability; by altering the interaction of CMR1 with the plasma membrane, or other molecules; or by affecting CMR1 protein activity. Compounds are screened, e.g., using high throughput screening (HTS), to identify those compounds that can bind to and/or modulate the activity of a CMR1 polypeptide or fragment thereof. In one embodiment, CMR1 proteins are recombinantly expressed in cells, e.g., human cells, and the modulation of CMR1 is assayed by using any measure of ion channel function, such as measurement of the membrane potential, or measures of changes in intracellular calcium levels. Alternatively, endogenous CMR1 in cells, e.g., human cells, can be used for the assays of the present invention. Methods of assaying ion, e.g., cation, channel function include, for example, patch clamp techniques, measurement of whole cell currents, and fluorescent imaging techniques that use $Ca^{2+}$-sensitive fluorescent dyes such as Fura-2.

Specific regions of the CMR1 nucleotide and amino acid sequences may be used to identify polymorphic variants, interspecies homologs, and alleles of CMR1 genes. Identification can be performed by using in vitro techniques, e.g., by using PCR under stringent or moderate hybridization conditions, or by using the sequence information in a computer system for comparison with other nucleotide sequences. Sequence comparison can be performed using any of the sequence comparison algorithms discussed herein below. Antibodies that bind specifically to CMR1 polypeptides or a conserved region thereof, can also be used to identify alleles, interspecies homologs, and polymorphic variants.

Nucleotide and amino acid sequence information for CMR1 are also used to construct models of CMR1 proteins. These models are subsequently used to identify compounds that can activate or inhibit CMR1 proteins.

A CMR1 agonist identified as set forth in the current application can be used for a number of different purposes. For example, a CMR1 activator can be included as a flavoring or perfuming agent in foods, beverages, soaps, medicines, soaps, etc. They can also be used in medicaments to provide a cooling or soothing sensation.

CMR1 modulators can also be used to treat diseases or conditions associated with CMR1 activity, such as pain. Further, the nucleic acid and protein sequences in the current application can be used to diagnose such diseases or conditions.

Kits are also provided for carrying out the herein-disclosed diagnostic and therapeutic methods.

Definitions

The term "cold perception" or "cold sensation" as used herein is the ability to perceive or respond to cold stimuli. Such stimuli include cold or cool temperatures, e.g., temperatures less than about 30°, and naturally occurring or synthetic compounds such as menthol (Eccles, *J. Pharm. Pharmacol* 46:618-630, 1994), eucalyptol, icilin (Wei & Seid, *J. Pharm. Pharmacol.* 35:110-112, 1983) and the like that elicit a cold sensation.

The term "pain" refers to all categories of pain, including pain that is described in terms of stimulus or nerve response, e.g., somatic pain (normal nerve response to a stimulus such as cold or menthol) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine*, pp. 93-98 (Wilson et al., eds., 12th ed. 1991); Williams et al., *J. of Medicinal Chem.* 42:1481-1485 (1999), herein each incorporated by reference in their entirety).

"Somatic" pain, as described above, refers to a normal nerve response to a stimulus, often a noxious stimulus such as injury or illness, e.g., cold, heat, trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Cation channels" are a diverse group of proteins that regulate the flow of cations across cellular membranes. The ability of a specific cation channel to transport particular cations typically varies with the valency of the cations, as well as the specificity of the given channel for a particular cation.

"Homomeric channel" refers to a cation channel composed of identical alpha subunits, whereas "heteromeric channel" refers to a cation channel composed of two or more different types of alpha subunits. Both homomeric and heteromeric channels can include auxiliary beta subunits.

A "beta subunit" is a polypeptide monomer that is an auxiliary subunit of a cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The terms "CMR1" protein or fragment thereof, or a nucleic acid encoding "CMR1" or a fragment thereof refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a CMR1 nucleic acid or amino acid sequence of a CMR1 protein, e.g., SEQ ID NO:1 or 3; (2) specifically bind to antibodies, e.g., polyclonal antibodies, raised against an immunogen comprising an amino acid sequence of a CMR1 protein or immunogenic fragments thereof, and conservatively modified variants thereof; (3) specifically hybridize under stringent hybridization conditions to an anti-sense strand corresponding to a nucleic acid sequence (SEQ ID NO:2 or 4) encoding a CMR1 protein, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to a CMR1 nucleic acid, e.g., SEQ ID NO:2 or 4. The nucleic acid and amino acid sequences for rat CMR1 have been deposited under GenBank Accession No. AY072788 and NM_134371, see also McKemy et al., *Nature* 416:52-58 (2002) and SEQ ID NO:1 and 3 herein. The nucleic acid and amino acid sequences for human CMR1 have been deposited under GenBank Accession No. NM_024080 and AY090109, see also Tsavaler et al., *Cancer Res.* 61:3760-3769, 2001; U.S. Pat. No. 6,194,152, and WO 99/09166 and SEQ ID NO: 3 and 4 herein. The nucleic acid and amino acid sequences for mouse CMR1 have been deposited under GenBank Accession No. NM_134252, see also Peier et al., *Cell* 108:705-715 (2002).

A CMR1 polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. CMR1 proteins typically have calcium ion channel activity, i.e., they are permeable to calcium.

By "determining the functional effect" or "determining the effect on the cell" is meant assaying the effect of a compound that increases or decreases a parameter that is indirectly or directly under the influence of a CMR1 polypeptide e.g., functional, physical, phenotypic, and chemical effects. Such functional effects include, but are not limited to, changes in ion flux, membrane potential, current amplitude, and voltage gating, a as well as other biological effects such as changes in gene expression of CMR1 or of any marker genes, and the like. The ion flux can include any ion that passes through the channel, e.g., calcium, and analogs thereof such as radioisotopes. Such functional effects can be measured by any means known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties,.

"Inhibitors," "activators," and "modulators" of CMR1 polynucleotide and polypeptide sequences are used to refer to activating, inhibitory, or modulating molecules identified using in vitro and in vivo assays of CMR1 polynucleotide and polypeptide sequences. Inhibitors are compounds that, e.g., bind to, partially or totally block activity, decrease, prevent, delay activation, inactivate, desensitize, or down regulate the activity or expression of CMR1 proteins, e.g., antagonists. "Activators" are compounds that increase, open, activate, facilitate, enhance activation, sensitize, agonize, or up regulate CMR1 protein activity. Inhibitors, activators, or modulators also include genetically modified versions of CMR1 proteins, e.g., versions with altered activity, as well as naturally occurring and synthetic ligands, antagonists, agonists, peptides, cyclic peptides, nucleic acids, antibodies, antisense molecules, siRNA, ribozymes, small organic molecules and the like. Such assays for inhibitors and activators include, e.g., expressing CMR1 protein in vitro, in cells, cell extracts, or cell membranes, applying putative modulator compounds, and then determining the functional effects on activity, as described above.

Samples or assays comprising CMR1 proteins that are treated with a potential activator, inhibitor, or modulator are compared to control samples without the inhibitor, activator, or modulator to examine the extent of activation or migration modulation. Control samples (untreated with inhibitors) are assigned a relative protein activity value of 100%. Inhibition of CMR1 is achieved when the activity value relative to the control is about 80%, preferably 50%, more preferably 25-0%. Activation of CMR1 is achieved when the activity value relative to the control (untreated with activators) is 110%, more preferably 150%, more preferably 200-500%

(i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, siRNA, oligonucleotide, ribozyme, etc., to be tested for the capacity to modulate cold sensation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequences SEQ ID NO:1), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or doublestranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated.

Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of β-sheet and α-helices. "Tertiary structure"

refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, Nature 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988) and Harlow & Lane, *Using Antibodies, A Laboratory Manual* (1999); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., Nature 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to CMR1 protein as encoded by SEQ ID NO:1, polymorphic variants, alleles, orthologs, and conservatively modified variants, or splice variants, or portions thereof, can be selected to obtain only those polyclonal antibodies that are specifically immunoreactive with CMR1 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, The Art, *Science and Technology of Pharmaceutical Compounding* (1999); and Pickar, *Dosage Calculations* (1999)).

Isolation of Nucleic Acids Encoding CMR1 Proteins

This invention relies on routine techniques in the field of recombinant genetics. Basic texts disclosing the general methods of use in this invention include Sambrook and Russell, Molecular Cloning, *A Laboratory Manual* (3rd ed. 2001); Kriegler, *Gene Transfer and Expression: A Laboratory Manual* (1990); and *Current Protocols in Molecular Biology* (Ausubel et al., eds., 1994)).

CMR1 nucleic acids, polymorphic variants, orthologs, and alleles that are substantially identical to an amino acid sequence encoded by SEQ ID NO:1, as well as other CMR1 family members, can be isolated using CMR1 nucleic acid probes and oligonucleotides under stringent hybridization conditions, by screening libraries. Alternatively, expression libraries can be used to clone CMR1 protein, polymorphic variants, orthologs, and alleles by detecting expressed homologs immunologically with antisera or purified antibodies made against human CMR1 or portions thereof.

To make a cDNA library, one should choose a source that is rich in CMR1 RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating CMR1 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human CMR1 directly from mRNA, from cDNA, from genomic libraries or cDNA libraries. Degenerate oligonucleotides can be designed to amplify CMR1 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of CMR1 encoding mRNA in physiological samples, for nucleic acid sequencing, or for other purposes. Genes amplified by the PCR reaction can be purified from agarose gels and cloned into an appropriate vector.

Gene expression of CMR1 can also be analyzed by techniques known in the art, e.g., reverse transcription and amplification of mRNA, isolation of total RNA or poly A' RNA, northern blotting, dot blotting, in situ hybridization, RNase protection, high density polynucleotide array technology, e.g., and the like.

Nucleic acids encoding CMR1 protein can be used with high density oligonucleotide array technology (e.g., GeneChip™) to identify CMR1 protein, orthologs, alleles, conservatively modified variants, and polymorphic variants in this invention. In the case where the homologs being identified are linked to modulation of T cell activation and migration, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene for CMR1 is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding CMR1, one typically subclones CMR1 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al., supra. Bacterial expression systems for expressing the CMR1 protein are available in, e.g., *E. coli, Bacillus* sp., and *Salmonella* (Palva et al., *Gene* 22:229-235 (1983); Mosbach et al., *Nature* 302: 543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the CMR1-encoding nucleic acid in host cells. A typical expression cassette thus contains a promoter operably linked to the nucleic acid sequence encoding CMR1 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/ $A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a CMR1 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of CMR1 protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing CMR1.

After the expression vector is introduced into the cells, the transfected cells are cultured under conditions favoring expression of CMR1, which is recovered from the culture using standard techniques identified below.

Purification of CMR1 Polypeptides

Either naturally occurring or recombinant CMR1 can be purified for use in functional assays. Naturally occurring CMR1 can be purified, e.g., from human tissue. Recombinant CMR1 can be purified from any suitable expression system.

The CMR1 protein may be purified to substantial purity by standard techniques, including selective precipitation with such substances as ammonium sulfate; column chromatography, immunopurification methods, and others (see, e.g., Scopes, *Protein Purification Principles and Practice* (1982); U.S. Pat. No. 4,673,641; Ausubel et al., supra; and Sambrook et al., supra).

A number of procedures can be employed when recombinant CMR1 protein is being purified. For example, proteins having established molecular adhesion properties can be reversible fused to the CMR1 protein. With the appropriate ligand, CMR1 protein can be selectively adsorbed to a purification column and then freed from the column in a relatively pure form. The fused protein is then removed by enzymatic activity. Finally, CMR1 protein could be purified using immunoaffinity columns.

A. Purification of CMR1 from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of CMR1 protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human CMR1 proteins are separated from other bacterial proteins by standard separation techniques, e.g., with Ni-NTA agarose resin.

Alternatively, it is possible to purify CMR1 protein from bacteria periplasm. After lysis of the bacteria, when the CMR1 protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying CMR1 Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the CMR1 proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The CMR1 proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays For Modulators Of CMR1 Protein

A. Assays

Modulation of a CMR1 protein, and corresponding modulation of lymphocyte activation and/or migration, can be assessed using a variety of in vitro and in vivo assays, including cell-based models as described above. Such assays can be used to test for inhibitors and activators of CMR1 protein or fragments thereof, and, consequently, inhibitors and activators of cold sensation. Such modulators of CMR1 protein are useful for creating a perception of coolness, e.g., for use in medications or as flavorings, or treating disorders related to cold perception. Modulators of CMR1 protein are tested using either recombinant or naturally occurring CMR1.

Often, the CMR1 protein will have the sequence as encoded by SEQ ID NO:1, or a human ortholog such as TRPM-8 (e.g., U.S. Pat. No. 6,194,152 and WO 99/09166) or a conservatively modified variant thereof. Alternatively, the CMR1 protein of the assay will be derived from a eukaryote and include an amino acid subsequence having substantial amino acid sequence identity to SEQ ID NO:1. Generally, the amino acid sequence identity will be at least 60%, preferably at least 65%, 70%, 75%, 80%, 85%, or 90%, most preferably at least 95%, e.g., 96%, 97%, 98% or 99%.

Measurement of cold sensation phenotype of CMR1 protein or cell expressing CMR1 protein, either recombinant or naturally occurring, can be performed using a variety of assays, in vitro, in vivo, and ex vivo, as described herein. To identify molecules capable of modulating CMR1, assays are performed to detect the effect of various candidate modulators on CMR1 activity in a cell.

The channel activity of CMR1 proteins can be assayed using a variety of assays to measure changes in ion fluxes including patch clamp techniques, measurement of whole cell currents, radiolabeled ion flux assays, and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Hoevinsky et al., *J. Membrane Biol.* 137:59-70 (1994)). For example, a nucleic acid encoding a CMR1 protein or homolog thereof can be injected into *Xenopus* oocytes. Channel activity can then be assessed by measuring changes in membrane polarization, i.e., changes in membrane potential. One means to obtain electrophysiological measurements is by measuring currents using patch clamp techniques, e.g., the "cell-attached" mode, the "inside-out" mode, and the "whole cell" mode (see, e.g., Ackerman et al., *New Engl. J. Med.* 336:1575-1595, 1997). Whole cell currents can be determined using standard methodology such as that described by Hamil et al., *PFlugers. Archiv.* 391:185 (1981).

Channel activity is also conveniently assessed by measuring changes in intracellular $Ca^{2+}$ levels. Such methods are well known in the art. For example, calcium flux can be measured by assessment of the uptake of $^{45}Ca^{2+}$ or by using fluorescent dyes such as Fura-2. In a typical microfluorimetry assay, a dye such as Fura-2, which undergoes a change in fluorescence upon binding a single $Ca^{2+}$ ion, is loaded into the cytosol of CMR-1-expressing cells. Upon exposure to CMR1 agonist, an increase in cytosolic calcium is reflected by a change in fluorescence of Fura-2 that occurs when calcium is bound.

The activity of CMR1 polypeptides can be also assessed using a variety of other in vitro and in vivo assays to determine functional, chemical, and physical effects, e.g., measuring the binding of CMR1 to other molecules, including peptides, small organic molecules, and lipids; measuring CMR1 protein and/or RNA levels, or measuring other aspects of CMR1 polypeptides, e.g., transcription levels, or physiological changes that affects CMR1 activity. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway. Such assays can be used to test for both activators and inhibitors of KCNB proteins. Modulators thus identified are useful for, e.g., many diagnostic and therapeutic applications.

In vitro assays

Assays to identify compounds with CMR1 modulating activity can be performed in vitro. Such assays can use full length CMR1 protein or a variant thereof (see, e.g., SEQ ID NO:1), or a fragment of a CMR1 protein, such as an extracellular domain or a cytoplasmic domain, optionally fused to a heterologous protein to form a chimera. In one embodiment, the full-length polypeptide can be used in high throughput binding assays to identify compounds that modulate cold sensation. Purified recombinant or naturally occurring CMR1 protein can be used in the in vitro methods of the invention. In addition to purified CMR1 protein or fragment thereof, the recombinant or naturally occurring CMR1 protein can be part of a cellular lysate or a cell membrane. As described below, the binding assay can be either solid state or soluble. Preferably, the protein, fragment thereof or membrane is bound to a solid support, either covalently or non-covalently. Often, the in vitro assays of the invention are ligand binding or ligand affinity assays, either non-competitive or competitive (with known extracellular ligands such as menthol). Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the CMR1 protein or fragment thereof is contacted with a potential modulator and incubated for a suitable amount of time. In one embodiment, the potential modulator is bound to a solid support, and the CMR1 protein is added. In another embodiment, the CMR1 protein is bound to a solid support. A wide variety of modulators can be used, as described below, including small organic molecules, peptides, antibodies, and CMR1 ligand analogs. A wide variety of assays can be used to identify CMR1-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for the CMR1 family are known (e.g., menthol). Either the modulator or the known ligand is bound first, and then the competitor is added. After the CMR1 protein is washed, interference with binding, either of the potential modulator or of the known ligand, is determined. Often, either the potential modulator or the known ligand is labeled.

High throughput functional genomics assays can also be used to identify modulators of cold sensation by identifying compounds that disrupt protein interactions between CMR1 and other proteins to which it binds. Such assays can, e.g., monitor changes in cell surface marker expression, changes in intracellular calcium, or changes in membrane currents using either cell lines or primary cells. Typically, the cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the phenotype of the cells is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., CMR1) can be isolated using a yeast two-hybrid system, mammalian two hybrid system, or phage display screen, etc. Targets so identified can be further used as bait in these assays to identify additional components that may interact with the CMR1 channel which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Cell-based in vivo Assays

In another embodiment, CMR1 protein is expressed in a cell, and functional, e.g., physical and chemical or phenotypic, changes are assayed to identify CMR1 modulators that modulate cold sensations. Cells expressing CMR1 proteins can also be used in binding assays. Any suitable functional effect can be measured, as described herein. For example, changes in membrane potential, changes in intracellular $Ca^{2+}$ levels, and ligand binding are all suitable assays to identify potential modulators using a cell based system. Suitable cells for such cell based assays include both primary cells, e.g., sensory neurons from the dorsal root ganglion and cell lines that express a CMR1 protein. The CMR1 protein can be naturally occurring or recombinant. Also, as described above, fragments of CMR1 proteins or chimeras with ion channel activity can be used in cell based assays. For example, a transmembrane domain of a CMR1 protein can be fused to a cytoplasmic domain of a heterologous protein, preferably a heterologous ion channel protein. Such a chimeric protein would have ion channel activity and could be used in cell based assays of the invention. In another embodiment, a domain of the CMR1 protein, such as the extracellular or cytoplasmic domain, is used in the cell-based assays of the invention.

In another embodiment, cellular CMR1 polypeptide levels are determined by measuring the level of protein or mRNA. The level of CMR1 protein or proteins related to CMR1 ion channel activation are measured using immunoassays such as western blotting, ELISA and the like with an antibody that selectively binds to the CMR1 polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, CMR1 expression can be measured using a reporter gene system. Such a system can be devised using a CMR1 protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to signal transduction can be measured. An activated or inhibited CMR1 will alter the properties of target enzymes, second messengers, channels, and other effector proteins. The examples include the activation of phospholipase C and other signaling systems. Downstream consequences can also be examined such as generation of diacyl glycerol and IP3 by phospholipase C.

Assays for CMR1 activity include cells that are loaded with ion or voltage sensitive dyes to report receptor activity, e.g., by observing calcium influx or intracellular calcium release. Assays for determining activity of such receptors can also use known agonists and antagonists for CMR1 receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog.

Animal Models

Animal models of cold sensation also find use in screening for modulators of lymphocyte activation or migration. Similarly, transgenic animal technology including gene knockout technology, for example as a result of homologous recombination with an appropriate gene targeting vector, or gene overexpression, will result in the absence or increased expression of the CMR1 protein. The same technology can also be applied to make knock-out cells. When desired, tissue-specific expression or knockout of the CMR1 protein may be necessary. Transgenic animals generated by such methods find use as animal models of cold responses.

Knock-out cells and transgenic mice can be made by insertion of a marker gene or other heterologous gene into an endogenous CMR1 gene site in the mouse genome via homologous recombination. Such mice can also be made by substituting an endogenous CMR1 with a mutated version of the CMR1 gene, or by mutating an endogenous CMR1, e.g., by exposure to known mutagens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual* (1988) and *Teratocarcinomas and Embryonic Stem Cells: A Practical Approach* (Robertson, ed., 1987).

B. Modulators

The compounds tested as modulators of CMR1 protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an CMR1 protein. Typically, test compounds will be small organic molecules, peptides, lipids, and lipid analogs. In one embodiment, the compound is a menthol analog, either naturally occurring or synthetic.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md.).

C. Solid State and Soluble High Throughput Assays

In one embodiment the invention provides soluble assays using a CMR1 protein, or a cell or tissue expressing a CMR1 protein, either naturally occurring or recombinant. In another embodiment, the invention provides solid phase based in vitro assays in a high throughput format, where the CMR1 protein or fragment thereof, such as the cytoplasmic domain, is attached to a solid phase substrate. Any one of the assays described herein can be adapted for high throughput screening, e.g., ligand binding, calcium flux, change in membrane potential, etc.

In the high throughput assays of the invention, either soluble or solid state, it is possible to screen up to several thousand different modulators or ligands in a single day. This methodology can be used for CMR1 proteins in vitro, or for cell-based or membrane-based assays comprising an CMR1 protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:5). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of CMR1 Polypeptides

In addition to the detection of CMR1 gene and gene expression using nucleic acid hybridization technology, one can also use immunoassays to detect CMR1 proteins of the invention. Such assays are useful for screening for modulators of CMR1 and lymphocyte activation and migration, as well as for therapeutic and diagnostic applications. Immunoassays can be used to qualitatively or quantitatively analyze CMR1 protein. A general overview of the applicable technology can be found in Harlow & Lane, *Antibodies: A Laboratory Manual* (1988).

A. Production of Antibodies

Methods of producing polyclonal and monoclonal antibodies that react specifically with the CMR1 proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of CMR1 protein may be used to produce antibodies specifically reactive with CMR1 protein. For example, recombinant CMR1 protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-CMR1 proteins, using a competitive binding immunoassay. Specific polyclonal antisera and monoclonal antibodies will usually bind with a $K_d$ of at least about 0.1 mM, more usually at least about 1 µM, preferably at least about 0.1 μM or better, and most preferably, 0.01 μM or better. Antibodies specific only for a particular CMR1 protein, such as human CMR1, can also be made, by subtracting out other cross-reacting CMR1 family members or orthologs from a species such as a non-human mammal. In this manner, antibodies that bind only to a particular CMR1 protein or ortholog may be obtained.

Once the specific antibodies against CMR1 protein are available, the protein can be detected by a variety of immunoassay methods. In addition, the antibody can be used therapeutically as a CMR1 modulators. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

CMR1 protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the CMR1 protein or antigenic subsequence thereof). The antibody (e.g., anti-CMR1) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled CMR1 or a labeled anti-CMR1 antibody. Alternatively, the labeling agent may be a third moiety, such a secondary antibody, that specifically binds to the antibody/CMR1 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting CMR1 in samples may be either competitive or noncompetitive. Noncompetitive immunoassays are assays in which the amount of antigen is directly measured. In one preferred "sandwich" assay, for example, the anti-CMR1 antibodies can be bound directly to a solid substrate on which they are immobilized. These immobilized antibodies then capture CMR1 present in the test sample. CMR1 proteins thus immobilized are then bound by a labeling agent, such as a second CMR1 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of CMR1 protein present in the sample is measured indirectly by measuring the amount of a known, added (exogenous) CMR1 protein displaced (competed away) from an anti-CMR1 antibody by the unknown CMR1 protein present in a sample. In one competitive assay, a known amount of CMR1 protein is added to a sample and the sample is then contacted with an antibody that specifically binds to CMR1 protein. The amount of exogenous CMR1 protein bound to the antibody is inversely proportional to the concentration of CMR1 protein present in the sample. In a particularly preferred embodiment, the antibody is immobilized on a solid substrate. The amount of CMR1 protein bound to the antibody may be determined either by measuring the amount of CMR1 present in CMR1 protein/antibody complex, or alternatively by measuring the amount of remaining uncomplexed protein. The amount of CMR1 protein may be detected by providing a labeled CMR1 molecule.

A hapten inhibition assay is another preferred competitive assay. In this assay the known CMR1 protein is immobilized on a solid substrate. A known amount of anti-CMR1 antibody is added to the sample, and the sample is then contacted with the immobilized CMR1. The amount of anti-CMR1 antibody bound to the known immobilized CMR1 is inversely proportional to the amount of CMR1 protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a CMR1 protein can be immobilized to a solid support. Proteins (e.g., CMR1 and homologs) are added to the assay that compete for binding of the antisera to the immobilized antigen. The ability of the added proteins to compete for binding of the antisera to the immobilized protein is compared to the ability of the CMR1 protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a CMR1 protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the CMR1 protein that is required to inhibit 50% of binding, then the second protein is said to specifically bind to the polyclonal antibodies generated to CMR1 immunogen.

Other Assay Formats

Western blot (immunoblot) analysis is used to detect and quantify the presence of CMR1 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind CMR1. The anti-CMR1 antibodies specifically bind to the CMR1 on the solid support. These antibodies may be directly labeled or alternatively may be subsequently detected using labeled antibodies (e.g., labeled sheep anti-mouse antibodies) that specifically bind to the anti-CMR1 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., 3H, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize CMR1 protein, or secondary antibodies that recognize anti-CMR1.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection

The present invention provides the nucleic acids of CMR1 protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a CMR1 protein of the present invention, thereby mitigating the effects of absent, partial inactivation, or abnormal expression of a CMR1 gene, particularly as it relates to cold sensation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Feigner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Bohm eds., 1995); and Yu et al., *Gene Therapy* 1:13-26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17th ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the CMR1 protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Menthol and Cold Activate an Inwardly Rectifying, $Ca^{2+}$-permeable Channel on Trigeminal Sensory Neurons Body surfaces that are innervated by trigeminal fibers, such as the eye and tongue, are particularly sensitive to cold and cooling compounds (e.g., Eccles, *J. Pharm. Pharmacol.* 46: 618-30 (1994)). Calcium imaging and electrophysiological methods were therefore used to examine responses of dissociated rat trigeminal neurons to menthol and cold. Indeed, these stimuli produced robust increases in intracellular free-calcium in a relatively small sub-population of trigeminal neurons (FIG. 1a), consistent with work from others using DRG cultures (see, e.g., Reid & Flonta, *Nature* 413:480 (2001); Suto & Gotoh, *Neuroscience* 92:1131-5 (1999); Okazawa et al., *Neuroreport* 11:2151-5 (2000)). Menthol and cold excited a largely overlapping subset of neurons, a significant fraction of which (54.5±6.1%) were also activated by capsaicin (FIG. 1a). Sensitivity to capsaicin is considered a functional hallmark of nociceptors (primary sensory neurons that detect noxious stimuli) and thus approximately half of the menthol/cold sensitive cells may be categorized as such.

Whole-cell patch-clamp recordings also showed that a subset of trigeminal neurons are sensitive to both menthol and cold (FIG. 1b). Thus exposure to these stimuli elicited rapidly developing membrane currents that were characterized by pronounced outward rectification (i.e., responses at positive holding potentials were substantially greater than those at negative voltages) (FIG. 1c). Menthol- or cold-evoked currents reversed close to 0 mV ($E_{rev}$=−3.56±1.90 mV and −0.82±0.25, respectively; n=5), suggesting that they result from the opening of non-selective cation channels, consistent with recent observations of cold responses in cultured DRG neurons (Reid & Flonta, supra). Ion substitution experiments further showed that these currents do not discriminate among monovalent cations, but exhibit significantly higher permeability for calcium ions ($P_{Ca}/P_{Na}$=3.22; $P_K/P_{Na}$=1.10; $P_{Cs}/P_K$=1.22; n=6) (FIG. 1d). We found these biophysical properties to be particularly interesting because they are reminiscent of VR1 and several other members of the TRP channel family (Clapham et al., *Nat. Rev. Neurosci.* 2:387-96 (2001)).

In trigeminal neurons, room temperature menthol evoked responses in a dose-dependent manner (FIG. 1e) with a half-maximal effective concentration ($EC_{50}$) of 80±2.4 mM, a potency that is within two-fold of that determined for DRG neurons using calcium imaging (Okazawa et al., supra). Fitting these data with the Hill equation suggests that receptor activation requires the binding of more than one menthol molecule (η=2.2). In addition to menthol, the mint plant synthesizes structural analogues that also elicit a cooling sensation, albeit with reduced potency. One of these, menthone, elicited very small currents in trigeminal neurons compared to an equivalent dose of menthol (FIG. 1b). Cyclohexanol, an inactive synthetic menthol analogue, had no effect. Cold also elicited membrane currents in these cells in a dose-dependent manner, with a characteristic temperature threshold of 27.1±0.5° C. (n=4) (FIG. 1f). As reported for DRG neurons, menthol potentiated cold responses and shifted the thermal threshold to higher temperatures (29.6±0.3° C. at 10 μM menthol). Conversely, increasing the temperature of perfusate (from room temperature to 30° C.) completely antagonized currents evoked by 100 mM menthol (FIG. 1b). Taken together, our findings and those of others demonstrate that menthol and cold activate a calcium permeable channel on DRG and trigeminal sensory neurons. Moreover, our electrophysiological data show that both stimuli activate currents with very similar biophysical properties, supporting the idea of a common molecular site of action.

Fluorescently labeled antibodies were used to identify cold/menthol receptor expressing cells in trigeminal ganglia. Cold/menthol receptor antibody and lectin IB4 specifically labeled subsets of rat trigeminal ganglia neurons.

Expression Cloning of a Receptor for Menthol and Other Cooling Compounds

Our electrophysiological studies demonstrate that menthol and cold activate native conductances with intrinsic and significant permeability to calcium ions. We therefore reasoned that a calcium imaging-based screening strategy, similar to that used for molecular identification of the vanilloid receptor (Caterina et al., *Nature* 389:816-24 (1997)) could be used to isolate a functional cDNA encoding a menthol or cold-sensitive receptor. In light of the higher prevalence of menthol- and cold-sensitive neurons in trigeminal ganglia (14.8% versus 7.4% for DRG, n=745 and 1425 cells, respectively), we constructed a cDNA expression library consisting of ~2 million independent clones from this tissue. Pools containing ~10, 000 clones were transfected into human embryonic kidney-derived HEK293 cells, which were subsequently loaded with the calcium-sensitive fluorescent dye, Fura-2, and microscopically examined for stimulus-evoked changes in intracellular calcium. We chose room temperature menthol (500 μM) as the agonist because of the technical simplicity in using a pharmacological, rather than a thermal stimulus for library screening. In this way, we identified a cDNA pool that conferred menthol sensitivity to a small proportion (<5%) of transfected cells. Iterative sub-division and re-screening ultimately yielded a single menthol-responsive clone.

As noted above, menthol is one of several naturally occurring or synthetic cooling compounds whose relative potencies in psychophysical or electrophysiological assays span a wide range (Eccles, *J. Pharm. Pharmacol.* 46:618-30 (1994)). To determine how the newly identified receptor responds to these compounds, we expressed the cloned cDNA in *Xenopus* oocytes and measured electrophysiological responses to these compounds using whole-cell voltage-clamp methods. Robust responses were evoked by menthol or by the super-cooling agent AG-3-5 (icilin) (see, e.g., Wei & Seid, *J. Pharm. Pharmacol.* 35:110-112 (1983)) with icilin showing nearly 200-fold greater potency than menthol ($EC_{50}$=0.36±0.03 μM and 66.7±3.3 μM, respectively). Icilin also activated the receptor with significantly greater efficacy (~2.5-fold) compared to menthol (FIG. 2a, b). Eucalyptol, the main constituent of oil of *Eucalyptus*, also elicited membrane currents, but with very decreased potency (3.4±0.4 mM) and efficacy compared to menthol or icilin. Menthone, camphor, and the inactive menthol analogue, cyclohexanol, had little or no effect, even when applied at concentrations approaching their limits of solubility in aqueous buffers (>500 μM). Finally, the vanilloid receptor agonist, capsaicin, did not elicit responses in these cells.

A more detailed biophysical analysis of the cloned receptor was carried out in transfected HEK293 cells, where menthol or icilin produced currents with nearly time-independent kinetics and steep outward rectification (FIG. 3a). Ion substitution experiments showed that, like native menthol-evoked responses in trigeminal neurons, these currents showed relatively high permeability to calcium and little selectivity among monovalent cations ($P_{Ca}/P_{Na}$=3.34; $P_K/P_{Na}$=1.20; $P_{Cs}/P_K$=1.14; n=4-9) (FIG. 3b). We also found that menthol-evoked currents showed significant desensitization (53.9±1.7% decrease in peak current between the first and second application, n=3). Interestingly, this phenomenon was largely dependent on extracellular calcium since little desensitization (9.1±7%, n=3) was observed in nominally calcium-free bath solution (FIG. 3c). Icilin showed even stronger desensitization, but unlike menthol, this agonist was essentially inactive in the absence of extracellular calcium. Similar observations were obtained in oocytes (not shown). When measured at the single channel level (cell-attached patch configuration), menthol-evoked currents also showed pronounced outward rectification. These responses were characterized by brief, transient openings and had a slope conductance of 83±3 pS at positive potentials (FIG. 3d, e). We also observed events with smaller unitary currents, which may represent either subconductance states of the channel or openings that were too brief to be resolved in our analysis.

The Menthol Receptor is Also Activated by Cold

Figure 4A:
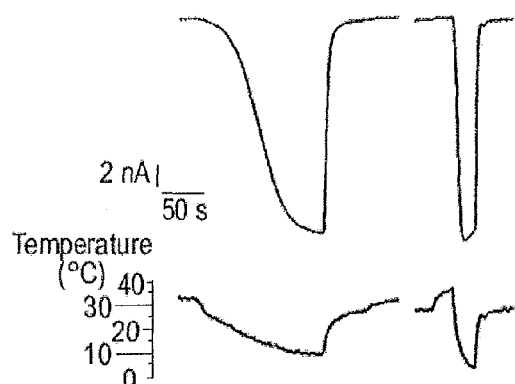
Figure 4B:
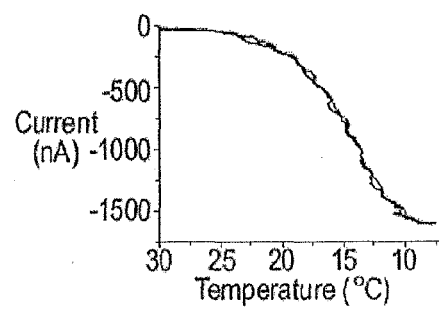
Figure 4C:
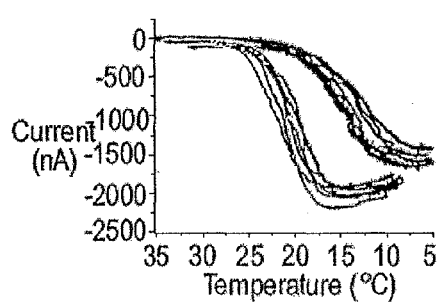
Figure 4D:
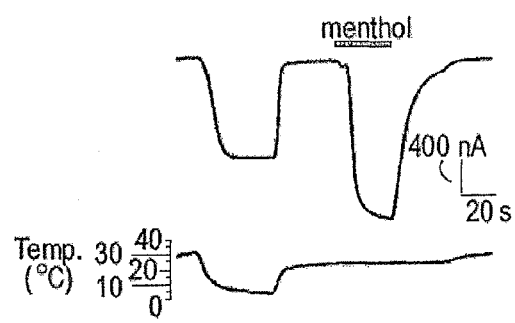
Figure 4E:
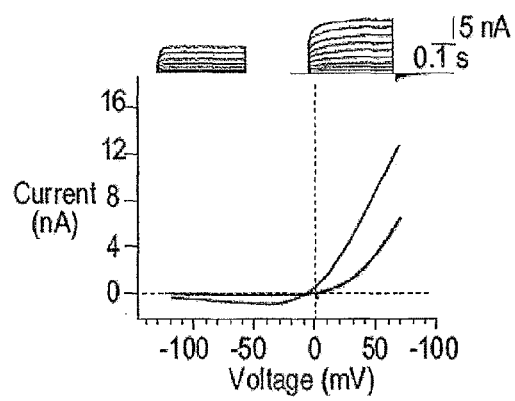

To determine whether the menthol receptor is also a cold sensor, we tested its thermal responsiveness in oocytes by lowering the temperature of the perfusate from ~35° C. to ~5° C. This elicited a robust and rapidly activating inward current (at negative holding potentials) that was remarkably consistent since the rate of temperature change (ranging from 0.2 to 1° C./second) did not influence threshold or saturation temperatures (FIG. 4a, b). Moreover, cold-evoked currents were directly proportional to temperature regardless of the direction of the temperature change (not shown). Cold-activated currents had a thermal threshold of 25.8±0.4° C. and saturated at 8.2±0.3° C. (n=12) (FIG. 4c). Consistent with the behavior of native cold currents, addition of a sub-activating concentration of menthol (20 mM) to the perfusate increased threshold and saturation temperature to 29.7±0.3° C. and 15.6±0.4° C., respectively (n=7) (FIG. 4c). Interestingly, we found that menthol is a more efficacious agonist than cold since saturating cold-evoked currents were of smaller magnitude than those obtained with a maximal dose of room temperature menthol (67.4±1.9%, n=7) (FIG. 4d).

Figure 4F:
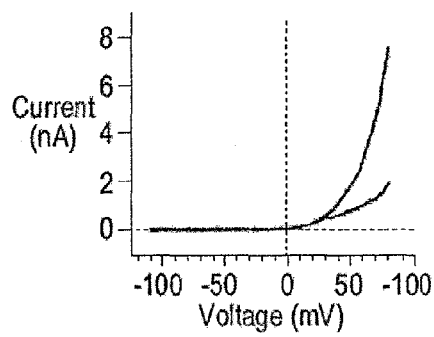

We also examined cold-evoked currents in menthol receptor-expressing HEK293 cells. As observed for native cold responses (FIG. 1c), current-voltage relationships for the cloned channel showed steep outward rectification (FIG. 4e) and were markedly potentiated by a sub-activating dose of menthol (10 µM). Menthol increased cold-evoked currents in both the outward and inward direction, but the effect on the inward component was more pronounced, reminiscent of the effect of capsaicin on VR1. Native cold-evoked responses in sensory fibers or cultured DRG neurons show adaptation to a prolonged thermal stimulus lasting several minutes (Reid & Flonta, supra; Kenshalo & Duclaux, *J. Neurophysiol.* 40:319-32 (1977)). We found that receptor-transfected cells showed small outwardly rectifying basal currents at room temperature (~22° C.), but that responses to a subsequent 22° C. stimulus were markedly larger after the cell had first been warmed to 31° C. (FIG. 4f). This observation suggests that the cloned receptor also shows adaptation to thermal challenges that can be reversed upon heating to room temperature. Desensitization to cold differed from that observed with menthol because it was independent of extracellular calcium (not shown). Interestingly, VR1 shows similar behavior in that desensitization to chemical (capsaicin) or thermal (heat) stimuli are calcium-dependent and -independent, respectively. Taken together, our observations show that the cloned receptor, which we now designate cold-menthol receptor subtype 1 (CMR1), has properties identical to endogenous cold/menthol currents observed in sensory neurons from trigeminal ganglia, as shown here, or from dorsal root ganglia (Reid & Flonta, supra; Suto & Gotoh, supra; Okazawa et al., supra).

CMR1 is a Member of the TRP Ion Channel Family

The CMR1 cDNA sequence includes an open reading frame of 3312 by that is predicted to encode a protein of 1104 amino acids with a molecular mass of 128 kD (FIG. 5a). Database searches revealed significant homology between this deduced sequence and members of the transient receptor potential (TRP) ion channel family. Within this family, CMR1 most closely resembles the subgroup of long TRP channels, so named for their characteristically large N- and C-terminal cytoplasmic tails compared to other TRP family members (Clapham et al., *Nat. Rev. Neurosci.* 2:387-96 (2001); Harteneck et al., *Trends Neurosci.* 23:159-66 (2000)). Long TRP channels are also termed TRPM in reference to melastatin, the founding member of this TRP channel subgroup initially identified in melanocytes and whose expression is downregulated in melanocystic tumors (Duncan et al., *Cancer Res.* 58:1515-20 (1998)). Among members of this subfamily, TRPM2 and TRPM7 have been electrophysiologically characterized and shown to behave as bifunctional proteins in which enzymatic activities associated with their long C-terminal domains are believed to regulate channel opening. Specifically, TRPM2 contains a Nudix motif associated with adenosine-5'-diphosphoribose (ADPR) pyrophosphatase activity and is gated by cytoplasmic ADPR and nicotinamide adenine dinucleotide (NAD) (Perraud et al., *Nature* 411:595-9 (2001) Sano et al., *Science* 293:1327-30 (2001)). TRPM7 contains a protein kinase domain that is required for channel activation (Runnels et al., *Science* 291:1043-7 (2001)). In contrast, CMR1 has a significantly shorter C-terminal region (FIG. 5b) and does not contain any obvious enzymatic domains that might be associated with channel regulation.

CMR1 is 92% identical to human TRPM8 (or trp-p8), a recently identified member of the TRPM subfamily (Tsavaler et al., *Cancer Res.* 61:3760-9 (2001)). Among normal tissues examined, TRPM8 was found to be expressed exclusively in prostate epithelia, as well as in a variety of tumors, including prostate, melanoma, colorectal, and breast carcinoma. The presence of this channel in sensory neurons was not assessed and we therefore carried out northern blot and in situ hybridization studies to examine expression of CMR1 in rat trigeminal and dorsal root ganglia. Indeed, transcripts of ~6 and 5 kb were detected in both neuronal tissues (FIG. 6a). At the cellular level, CMR1 transcripts were found in a subset of sensory neurons with small-diameter cell bodies (18.2±1.1 mm and 21.6±0.5 mm in dorsal root and trigeminal ganglia, respectively) (FIG. 6b), similar in size to VR1-expressing cells (19.2±0.3 mm) (Caterina et al., *Nature* 398:436-41 (1999)). Consistent with calcium imaging and patch-clamp studies, a subset of small-diameter neurons were labeled by the CMR1 probe and expression was conspicuously absent from the vast majority of larger-diameter cells. CMR1 transcripts were more prevalent in trigeminal ganglia versus dorsal root ganglia, which is also consistent with the physiological observations using neuronal cultures. Taken together, these findings suggests that within sensory ganglia, CMR1 is expressed by a sub-population of primary afferent fibers (C & Aδ).

Thus, cooling compounds and cold are detected by the same molecular entity, CMR1, on primary afferent neurons of the somatosensory system. Moreover, thermosensation over a wide temperature range is mediated by a common molecular mechanism that uses TRP ion channels as primary transducers of thermal stimuli. For example, as few as three ion channels (CMR1, VR1, and VRL-1) may provide coverage for a r wide range of temperatures (e.g., 8 to 28° C., >43° C., and >50° C., respectively) (FIG. 7a).

Methods

Neuronal Cell Culture and Ca2+ Microfluorimetry

Trigeminal ganglia were removed from newborn S/D rats, placed in ice-cold culture medium (MEM Eagle's with Earle's BSS supplemented with 10% horse serum, vitamins, penicillin/streptomycin and L-glutamine), cleaned of connective tissue/blood vessels and diced into 4-5 pieces. Ganglia were then transferred to 0.125% collagenase P (Boehringer) solution in CMF Hank's, shaken gently at 37° C. for 20 (P0 animals) to 30 min (P4 animals), pelleted, and resuspended in 0.05% STV at 37° C. for 2 min. Culture medium was added to inhibit enzymatic activity and ganglia were triturated gently with a fire-polished Pasteur pipette. Neurons were enriched by density gradient centrifugation as described (see, e.g., Eckert et al., *J. Neurosci. Methods* 77:183-90, 1997). Cells were resuspended in complete culture medium (MEM Eagle's/Earle's BSS with 10% horse serum, vitamins, penicillin/streptomycin, L-glutamine and 100 ng/ml NGF 7S (Invitrogen) and plated onto glass coverslips coated with PLO (1 mg/ml, Sigma) and laminin (5 µg/ml, Invitrogen). Cultures were maintained at 37° C. in 5% CO2 and examined 1-2 days after plating. $Ca^{2+}$ microfluorimetry was carried out as described (Caterina et al., *Nature* 389:816-24 (1997)). For cell selection prior to patch-clamp analysis, $CaCl_2$ and pluronic acid were omitted from the loading buffer (nominally $Ca^{2+}$-free CIB). Cells in the recording chamber were perfused by gravity using the VC-6 valve control system (Warner Inst.).

Mammalian Cell Electrophysiology

Trigeminal neurons responding to 50 mM menthol with an increase in intracellular $Ca^{2+}$ were selected for patch-clamp recordings. HEK293 cells were cultured in DMEM with 10% fetal bovine serum and co-transfected (Lipofectamine 2000, Invitrogen) with 1 µg CMRi plasmid and 0.1 µg enhanced green fluorescence reporter plasmid to identify transfected cells. Cells were plated onto PLO-coated coverslips the next day and examined two days after transfection. Gigaseals were formed with pipettes (Garner Glass type 7052, ID 1.1, OD 1.5) having a resistance of 3-5 MΩ in standard pipette solution. Whole-cell voltage clamp was performed at a holding potential of −60 mV with a 200 ms voltage ramp from −120 mV to +80 mV at 3.6 Hz. Data were acquired using Pulse-Pulsefit (HEKA GmbH) software. Recordings were filtered at 5 kHz and sampled at 20 kHz. Pipette solution for neuronal experiments contained (in mM) 140 CsCl, 1 EGTA, 0.6 $MgCl_2$, 10 HEPES, pH 7.4 (adjusted with CsOH). Standard $Ca^{2+}$-free bath solution for whole-cell recordings contained (in mM) 140 NaCl, 4 KCl, 2 $MgCl_2$, 100 nM TTX (Sigma), 10 TRIS, pH 7.4 (adjusted with HCl) with or without 100 nM dendrotoxin I (Sigma). For ion replacement experiments, pipette solution contained (in mM) 140 KCl, 5 CsCl, 1 EGTA, 0.6 $MgCl_2$, 1 4-aminopyridine, 10 HEPES, pH 7.4 (adjusted with KOH). Bath solution contained (in mM) 140 NaCl, 4 KCl, 2 $MgCl_2$, 100 nM TTX, 100 nM dendrotoxin 1,100 nM apamine (Sigma), 100 nM carybdotoxin (Sigma), 1 µM ω-conotoxin MVIIC, 1 µM GVIA (Latoxan), 10 TRIS, pH 7.4 (adjusted with HCl). For monovalent cation permeability experiments perfusate contained (in mM) 140 NaCl (or 140 KCl or 140 NMDG), 100 nM TTX, 1 µM nitrendipine (Sigma), 10 HEPES, 10 glucose, pH 7.4 (adjusted with NaOH, KOH or HCl, respectively). For divalent cation permeability experiments perfusate contained (in mM) 125 NMDG, 10 $CaCl_2$, 100 nM TTX, 1 µM nitrendipine, 10 HEPES, 10 glucose, pH 7.4 (adjusted with HCl). Liquid junction potentials (measured directly in separate experiments) did not exceed 3 mV and thus no correction for this offset was made. Bath solution for on-cell single channel experiments contained (in mM): 150 NaCl, 1 $MgCl_2$, 10 TRIS. Pipette solution for on-cell single channel experiments contained (in mM): 150 NaCl, 1 $MgCl_2$, 0.1 EGTA, 10 TRIS and 5 or 25 µM menthol. Recordings were performed at 22° C. unless noted otherwise. Temperature ramps were generated by cooling or heating the perfusate in a jacketed coil (Harvard Inst.) connected to a thermostat. Temperature in the proximity of the patched cell was measured using a miniature thermocouple (type MT-29/2, Physitemp) and sampled using an ITC-18 A/D board (Instrutech) and Pulse software. Permeability ratios for monovalent cations to Na ($P_x/P_{Na}$) were calculated according to: $P_x/P_{Na} = \exp(\Delta E_{rev(Na-X)}F/RT)$, where $\Delta E r_{ev(Na-x)}$ equals the reversal potential change, F the Faraday's constant, R the universal gas constant and T the absolute temperature. For measurements of $Ca^{2+}$ permeability $P_{Ca}/P_{Na}$ was calculated according to Lewis, C. A. *J. Physiol.* 286:417-45, 1979, (equation A6).

Expression Cloning, Northern Blot Analysis and In Situ Hybridization

Trigeminal neurons from newborn rats were dissociated and enriched as described Eckert, supra. Polyadenylated RNA (~2 µg) was isolated from these cells (PolyA Tract Kit, Promega) and used to construct a cDNA library in pcDNA3 (Invitrogen) as described (Brake et al., *Nature* 371:519-23 (1994)). Library subpools consisting of ~10,000 clones were transiently transfected into HEK293 cells by lipofection and split 24 hours later into 8-well glass chamber slides coated with Matrigel (Becton-Dickinson). Responses to chemical or thermal stimuli were assessed 6-24 hours later by Fura-2 $Ca^{2+}$-imaging. Northern blotting and in situ hybridization histochemistry were performed as described (Caterina et al., *Nature* 389:816-24 (1997)) using the entire CMR1 cDNA to generate $^{32}P$— or digoxygenin-labeled probes, respectively.

Oocyte Electrophysiology cRNA transcripts were synthesized and injected into *Xenopus laevis* oocytes as described (Brake, supra). Two-electrode voltage-clamp recordings were performed 2-7 days post-injection. Dose-response curves for cooling compounds were performed at room temperature (22-24° C.). AG-3-5 (icilin) was provided by Dr. E. Wei, University of California, Berkeley. Temperature ramps were generated by heating (~35° C.) or cooling (~4° C.) the perfusate in a Harvard coil and monitoring temperature changes with a thermister placed near the oocyte.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A method for identifying a compound that modulates a cool or cold sensation in a mammalian subject, the method comprising:
   (i) contacting a cell comprising a cold- and menthol-sensitive receptor (CMR1) polypeptide with the compound, wherein the CMR1 polypeptide comprises a sequence having at least 90% identity to SEQ ID NO:3 and forms a cation channel; and
   (ii) determining whether said compound that modulates the activity of said CMR1 polypeptide based on an effect in said cell that correlates to CMR1 activity, and
   (iii) if said compound elicits the effect in said cell, further determining whether said compound modulates a cool/cold sensation in a mammalian subject, thereby identifying a compound that modulates cool or cold-sensation.

2. The method of claim 1, wherein the effect is a change in intracellular calcium.

3. The method of claim 2, wherein the effect is measured using a fluorescent compound.

4. The method of claim 1, wherein the effect is a change in membrane potential.

5. The method of claim 1, wherein the cell is a non-neuronal cell.

6. The method of claim 1, wherein the CMR1 is recombinant.

7. The method of claim 1, wherein the CMR1 polypeptide is encoded by a nucleic acid having at least 95% identity to SEQ ID NO: 4.

8. The method of claim 1, wherein the CMR1 polypeptide is encoded by a nucleic acid having at least 98% identity to SEQ ID NO: 4.

9. The method of claim 1, wherein the CMR1 polypeptide is encoded by a nucleic acid having the sequence set forth in SEQ ID NO: 4.

10. The method of claim 1, further comprising a step of stimulating the cell with cold temperature.

11. The method of claim 1, wherein the identified compound enhances cool or cold sensation.

12. The method of claim 1, wherein the identified compound inhibits cool or cold sensation.

13. The method of claim 1, wherein the cell is derived from mammalian cell lines 293 or CHO.

14. The method of claim 1, wherein the CMR1 polypeptide has at least 95% identity to SEQ ID NO: 3.

15. The method of claim 1, wherein the CMR1 polypeptide has at least 98% identity to SEQ ID NO: 3.

16. The method of claim 1, wherein the CMR1 polypeptide has the amino acid sequence set forth in SEQ ID NO: 3.

17. The method of claim 1, wherein said mammal is a human.

18. The method of claim 1, wherein the cation channel responds to cool or cold temperatures.

19. The method of claim 1, wherein the cation channel responds to a menthol compound.

* * * * *